United States Patent
Li et al.

(10) Patent No.: US 12,297,192 B2
(45) Date of Patent: May 13, 2025

(54) CRYSTAL FORM OF PYRIMIDINE SULFONAMIDE COMPOUND AND PREPARATION METHOD THEREFOR

(71) Applicant: WUXI BIOCITY BIOPHARMACEUTICS CO., LTD., Jiangsu (CN)

(72) Inventors: Junmiao Li, Shanghai (CN); Maoyi Lei, Shanghai (CN); Yunfu Luo, Shanghai (CN)

(73) Assignee: Wuxi Biocity Biopharmaceuticals Co., Ltd., Jiangsu (CN)

( * ) Notice: Subject to any disclaimer, the term of this patent is extended or adjusted under 35 U.S.C. 154(b) by 696 days.

(21) Appl. No.: 17/595,651

(22) PCT Filed: May 22, 2020

(86) PCT No.: PCT/CN2020/091737
§ 371 (c)(1),
(2) Date: Nov. 22, 2021

(87) PCT Pub. No.: WO2020/233694
PCT Pub. Date: Nov. 26, 2020

(65) Prior Publication Data
US 2022/0220098 A1    Jul. 14, 2022

(30) Foreign Application Priority Data
May 22, 2019   (CN) .......................... 201910428795.9

(51) Int. Cl.
C07D 405/14   (2006.01)
A61P 9/12   (2006.01)

(52) U.S. Cl.
CPC .............. *C07D 405/14* (2013.01); *A61P 9/12* (2018.01); *C07B 2200/13* (2013.01)

(58) Field of Classification Search
CPC .. C07D 405/14; C07D 405/04; C07B 2200/13
See application file for complete search history.

(56) References Cited

U.S. PATENT DOCUMENTS

2020/0283425 A1   9/2020   Luo et al.

FOREIGN PATENT DOCUMENTS

| CN | 109232546 A | 1/2019 |
|---|---|---|
| EA | 023864 B1 | 7/2016 |
| WO | 2002005355 A1 | 1/2002 |
| WO | 2002053557 A1 | 7/2002 |
| WO | 2007031933 A2 | 3/2007 |
| WO | 2011019630 A2 | 2/2011 |
| WO | 2019101039 A1 | 5/2019 |

OTHER PUBLICATIONS

International Search Report issued Aug. 14, 2020 in PCT/CN2020/091737.
Written Opinion issued Aug. 14, 2020 in PCT/CN2020/091737.
Examination Report issued in CA Application No. 3139553.
Byrn et al., "Pharmaceutical Solids: A Strategic Approach to Regulatory Considerations", Pharma. Res., 12/7, pp. 945-954, 1995.
Bavin, "Polymorphism in Process Development", Chemistry and Industry, pp. 527-529, Aug. 21, 1989.
Carlson et al., "An integrated high throughput workflow for pre-formulations: Polymorph and salt selection studies", Pharm. Chem, Drug Development, pp. 10-15, 2003.
Search Report issued Feb. 6, 2024 in Russian Application No. 2021135068.
Mino R. Caira, "Crystalline Polymorphism of Organic Compounds," Topics in Current Chemistry, vol. 198, pp. 163-208 (1998).
Bipul Sarma, "Solid forms of pharmaceuticals: Polymorphs, salts and cocrystals," Korean J. Chem. Eng., 28(2), pp. 315-322 (2011).
Narayan Variankaval, et al., "From Form to Function: Crystallization of Active Pharmaceutical Ingredients," AIChE Journal, vol. 54, No. 7, pp. 1682-1688, Jul. 2008.
Office Action issued in Israel Patent Application No. 288224, dated Aug. 14, 2024 [6 PAGES].
"Polymorphism in Pharmaceutical Solids," edited by Brittain HG, Marcel Dekker Inc., Grant DJW (chapter 1), Guillory JK (chapter 5), ISBN: 0-8247-0237-9, Dec. 1999 [95 PAGES].

*Primary Examiner* — Susanna Moore
(74) *Attorney, Agent, or Firm* — IceMiller LLP

(57) ABSTRACT

Disclosed are a Crystal Form (I) of a pyrimidine sulfonamide compound and a preparation method therefor. The present disclosure relates to an application thereof in the preparation of a medicament for treating diseases related to $ET_A$ receptor antagonists.

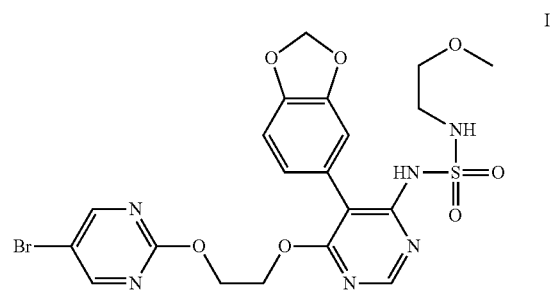

19 Claims, 3 Drawing Sheets

CRYSTAL FORM OF PYRIMIDINE SULFONAMIDE COMPOUND AND PREPARATION METHOD THEREFOR

CROSS-REFERENCE TO RELATED APPLICATION

This application is a Section 371 of International Application No. PCT/CN2020/091737 filed May 22, 2020, which was published in the Chinese language Nov. 26, 2020, under International Publication No. WO 2020/2336941 A1, which claims priority to Chinese Patent Application No. 201910428795.9 filed May 22, 2019, the disclosures of which are incorporated herein by reference in their entireties.

TECHNICAL FIELD

Provided are crystal forms of a pyrimidine sulfonamide compound and preparing process thereof, as well as use of the crystal forms for the manufacture of a medicament for treating a disease related to $ET_A$ receptor antagonists.

BACKGROUND

Endothelins (ETs) are a family of isopeptides containing 21 amino acids, all with a hydrophobic C-terminus consisting of six identical amino acid residues and two intra-chain disulfide bonds. There are three different genetically encoded isoforms occurring in the human body: ET-1, ET-2 and ET-3, among which ET-1 has the strongest vasoconstrictive activity. It induces three to ten times higher vasoconstrictive strength in veins than in arteries, and is the main isoform that underlies diseases. ET-1 is the most abundant and functionally important member of the endothelin family. It is mainly expressed in the vascular endothelium but is also found in non-vascular tissues of the heart, kidney, lung, adrenal glands and other organs.

ETs function not only as vascular factors in the regulation of blood pressure, but also as hormones in many cellular processes (such as proliferation, apoptosis and migration) leading to tissue hypertrophy, remodeling, fibrosis and inflammation. Elevated plasma and tissue levels of ET-1 are seen in a variety of diseases, for example, pulmonary hypertension, hypertension, sepsis, atherosclerosis, acute myocardial infarction, congestive heart failure, migraine and asthma, etc. Therefore, endothelin receptor antagonists have been extensively studied as very promising therapeutic agents.

Endothelin receptors belong to G protein-coupled receptors. Currently, there are mainly three known endothelin receptors, $ET_A$, $ET_B$ and $ET_C$, which show different distribution in different tissues and organs, and have different affinities for the three endothelin isoforms, and differ significantly in their physiological effects. Endothelin $ET_A$ receptor predominantly distributes on smooth muscle cells. It selectively binds to ET-1 and mediates the contraction of vascular smooth muscle. Endothelin $ET_B$ receptors can be divided into two subtypes, $ET_{B1}$ and $ET_{B2}$; the former distributes in endothelial cells and mediates the release of endothelium-derived relaxing factor (EDRF), prostacyclin ($PGI_2$) and nitric oxide (NO), causing vasodilation; and the latter are located on vascular smooth muscle and acts like $ET_A$ receptors, directly mediating venous vasoconstriction. Endothelin $ET_B$ receptors show comparable affinities for ET-1, ET-2 and ET-3. The $ET_C$ receptor is an ET-3 selective receptor that mainly distributes in neuronal cells and acts as a neurotransmitter. ET-1 acts mainly through $ET_A$ and $ET_B$ receptors. Endothelin receptor antagonists can be classified into three types: $ET_A$ receptor antagonists, $ET_B$ receptor antagonists and dual $ET_A/ET_B$ antagonists. The preclinical and/or clinical effects of endothelin receptor antagonists have been demonstrated on many diseases such as subarachnoid hemorrhage, heart failure, pulmonary hypertension, essential hypertension, refractory hypertension, neurogenic inflammation, diabetic nephropathy, focal segmental glomerulosclerosis, renal failure, neurogenic inflammation, and cerebral vasospasm following renal failure and myocardial infarction. Highly selective $ET_A$ receptor antagonists inhibit the strong vasoconstrictive effects of ET-1 while avoiding some of the adverse effects of non-selective dual $ET_A/ET_B$ receptor antagonists, thereby reducing clinical side effects.

Patent publication WO200205355 discloses the compound Macitentan, which can be used for the treatment of diseases associated with the effects of endothelins.

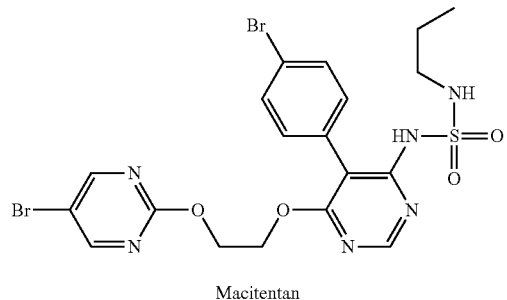 [SMILES: CCCNS(=O)(=O)Nc1ncnc(OCCOc2ncc(Br)cn2)c1-c1ccc(Br)cc1]

Macitentan

SUMMARY

Provided is a Crystal Form A of the compound as shown in formula (I), characterized in that, the Crystal Form A has an X-ray powder diffraction pattern having characteristic diffraction peaks at the following 2θ angles: 12.62±0.20°, 16.86±0.20°, 19.33±0.20°, and 25.38±0.20°.

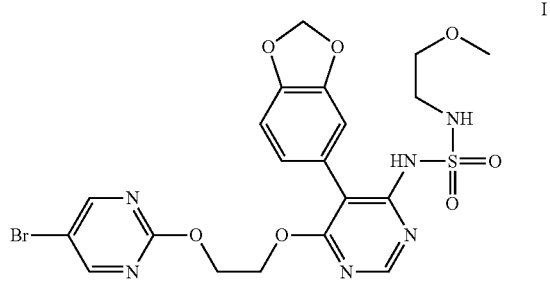 [SMILES: COCCNS(=O)(=O)Nc1ncnc(OCCOc2ncc(Br)cn2)c1-c1ccc2c(c1)OCO2]

In some embodiments of the present disclosure, the Crystal Form A has an X-ray powder diffraction pattern having characteristic diffraction peaks at the following 2θ angles: 8.42±0.20°, 10.31±0.20°, 12.62±0.20°, 16.86±0.20°, 18.28±0.20°, 19.33±0.2°, 21.87±0.20°, 25.38±0.20°, and 27.14±0.20°.

In some embodiments of the present disclosure, the Crystal Form A has an X-ray powder diffraction pattern having characteristic diffraction peaks at the following 2θ angles: 8.42±0.20°, 10.31±0.20°, 12.62±0.20°, 16.86±0.20°, 18.28±0.20°, 19.33±0.2°, 21.87±0.20°, 22.93±0.20°, 25.38±0.20°, 26.63±0.20°, and 27.14±0.20°.

In some embodiments of the present disclosure, the Crystal Form A has an X-ray powder diffraction pattern having characteristic diffraction peaks at the following 2θ angles: 8.42°, 9.41°, 9.58°, 9.82°, 10.31°, 12.62°, 15.77°, 16.62°, 16.86°, 17.51°, 17.97°, 18.28°, 18.85°, 19.33°, 19.58°, 20.33°, 21.87°, 22.58°, 22.93°, 23.15°, 23.39°, 25.05°, 25.38°, 26.31°, 26.63°, 27.14°, 27.79°, 29.40°, 31.01°, 31.48°, 35.42°, and 39.21°.

In some embodiments of the present disclosure, the Crystal Form A has an XRPD pattern as shown in FIG. 1.

In some embodiments of the present disclosure, the Crystal Form A has an XRPD pattern with analysis data as shown in Table 1.

TABLE 1

XRPD Pattern Analysis Data of Crystal Form A of the compound of formula (I)

| No. | 2θ angle (°) | Interplanar spacing (Å) | Relative intensity (%) |
|---|---|---|---|
| 1 | 8.417 | 10.496 | 10.2 |
| 2 | 9.406 | 9.3946 | 5.9 |
| 3 | 9.584 | 9.2203 | 4.4 |
| 4 | 9.822 | 8.9973 | 3.6 |
| 5 | 10.309 | 8.5741 | 8.6 |
| 6 | 12.623 | 7.0069 | 52.2 |
| 7 | 15.774 | 5.6136 | 3.4 |
| 8 | 16.624 | 5.3283 | 11 |
| 9 | 16.859 | 5.2547 | 32.4 |
| 10 | 17.514 | 5.0596 | 5.2 |
| 11 | 17.971 | 4.9318 | 5.8 |
| 12 | 18.278 | 4.8497 | 11.2 |
| 13 | 18.85 | 4.7039 | 3.4 |
| 14 | 19.327 | 4.5887 | 68.1 |
| 15 | 19.579 | 4.5302 | 4 |
| 16 | 20.328 | 4.3651 | 5.1 |
| 17 | 21.867 | 4.0612 | 14.4 |
| 18 | 22.579 | 3.9347 | 5.2 |
| 19 | 22.933 | 3.8748 | 13.4 |
| 20 | 23.152 | 3.8386 | 13 |
| 21 | 23.39 | 3.8001 | 4.6 |
| 22 | 25.047 | 3.5523 | 5.6 |
| 23 | 25.383 | 3.5061 | 100 |
| 24 | 26.314 | 3.3841 | 5.6 |
| 25 | 26.626 | 3.3451 | 12.2 |
| 26 | 27.135 | 3.2836 | 26.8 |
| 27 | 27.79 | 3.2076 | 6.1 |
| 28 | 29.403 | 3.0351 | 3.1 |
| 29 | 31.008 | 2.8817 | 6.5 |
| 30 | 31.475 | 2.8399 | 3.2 |
| 31 | 35.418 | 2.5323 | 4.8 |
| 32 | 39.207 | 2.2959 | 5.7 |

In some embodiments of the present disclosure, the Crystal Form A has a differential scanning calorimetry curve having the onset point of an endothermic peak at 161.3±3.0° C.

In some embodiments of the present disclosure, the Crystal Form A has a DSC pattern as shown in FIG. 2.

In some embodiments of the present disclosure, the Crystal Form A has a thermogravimetric analysis curve having a weight loss of 0.01% at 152.3±3.0° C.

In some embodiments of the present disclosure, the Crystal Form A has a TGA pattern as shown in FIG. 3.

Provided is a Crystal Form B of the compound as shown in formula (I), characterized in that, the Crystal Form B has an X-ray powder diffraction pattern having characteristic diffraction peaks at the following 2θ angles: 7.51±0.20°, 9.60±0.20°, and 22.56±0.20°.

Provided is a Crystal Form B of the compound as shown in formula (I), characterized in that, the Crystal Form B has an X-ray powder diffraction pattern having characteristic diffraction peaks at the following 2θ angles: 7.51±0.20°, 22.56±0.20°, and 24.79±0.20°.

Provided is a Crystal Form B of the compound as shown in formula (I), characterized in that, the Crystal Form B has an X-ray powder diffraction pattern having characteristic diffraction peaks at the following 2θ angles: 7.51±0.20°, 15.05±0.20°, 22.56±0.20°, and 24.79±0.20°.

In some embodiments of the present disclosure, the Crystal Form B has an X-ray powder diffraction pattern having characteristic diffraction peaks at the following 2θ angles: 7.51±0.20°, 9.60±0.20°, 15.05±0.20°, 19.09±0.20°, 22.56±0.20°, 24.18±0.20°, 24.79±0.20°, and 27.95±0.20°.

In some embodiments of the present disclosure, the Crystal Form B has an X-ray powder diffraction pattern having characteristic diffraction peaks at the following 2θ angles: 7.51±0.20°, 9.60±0.20°, 15.05±0.20°, 19.09±0.20°, 22.20±0.20°, 22.56±0.20°, 24.18±0.20°, 24.79±0.20°, and 27.95±0.20°.

In some embodiments of the present disclosure, the Crystal Form B has an X-ray powder diffraction pattern having characteristic diffraction peaks at the following 2θ angles: 7.51°, 9.60°, 11.08°, 15.05°, 15.52°, 17.53°, 18.34°, 19.09°, 20.41°, 20.85°, 22.20°, 22.56°, 23.15°, 24.18°, 24.79°, 27.69°, 27.95°, 28.75°, 33.57°, and 35.42°.

In some embodiments of the present disclosure, the Crystal Form B has an XRPD pattern as shown in FIG. 4.

In some embodiments of the present disclosure, the Crystal Form B has an XRPD pattern with analysis data as shown in Table 2.

TABLE 2

XRPD Pattern Analysis data of Crystal Form B of the compound of formula (I)

| No. | 2Θ angle (°) | Interplanar spacing (Å) | Relative intensity (%) |
|---|---|---|---|
| 1 | 7.513 | 11.7575 | 84.1 |
| 2 | 9.602 | 9.2036 | 38.3 |
| 3 | 11.078 | 7.9801 | 16.4 |
| 4 | 15.047 | 5.8829 | 60.9 |
| 5 | 15.515 | 5.7066 | 18.3 |
| 6 | 17.533 | 5.054 | 15.5 |
| 7 | 18.336 | 4.8345 | 23.5 |
| 8 | 19.088 | 4.6456 | 56.4 |
| 9 | 20.41 | 4.3476 | 19.4 |
| 10 | 20.845 | 4.2578 | 28.6 |
| 11 | 22.202 | 4.0006 | 60.9 |
| 12 | 22.562 | 3.9376 | 100 |
| 13 | 23.15 | 3.839 | 26.6 |
| 14 | 24.179 | 3.6778 | 43.1 |
| 15 | 24.789 | 3.5887 | 82.6 |
| 16 | 27.688 | 3.2192 | 20.1 |
| 17 | 27.946 | 3.1901 | 55.1 |
| 18 | 28.754 | 3.1022 | 19.8 |
| 19 | 33.567 | 2.6676 | 13.5 |
| 20 | 35.419 | 2.5322 | 16.6 |

In some embodiments of the present disclosure, the Crystal Form B has a differential scanning calorimetry curve having the onset point of an endothermic peak at 150.3±3.0° C.

In some embodiments of the present disclosure, the Crystal Form B has a DSC pattern as shown in FIG. 5.

In some embodiments of the present disclosure, the Crystal Form B has a thermogravimetric analysis curve having a weight loss of 0.53% at 90.0±3.0° C., and a further weight loss of 0.60% at 143.9±3.0° C.

In some embodiments of the present disclosure, the Crystal Form B has a TGA pattern as shown in FIG. 6.

In some embodiments of the present disclosure, provided is a process for preparing the Crystal Form A of the compound as shown in formula (I), comprising:
(1) adding the compound as shown in formula (I) into a solvent, with heating for dissolving;
(2) cooling the solution in (1) until a solid is precipitated; stirring; and filtering to give the Crystal Form A of the compound of formula (I).

In some embodiments of the present disclosure, in the preparation process, the solvent is selected from the group consisting of tetrahydrofuran and acetonitrile.

In some embodiments of the present disclosure, in the preparation process, the stirring is conducted at the temperature of 10° C. to 60° C.

In some embodiments of the present disclosure, in the preparation process, the stirring time is 12 hours to 24 hours.

In some embodiments of the present disclosure, in the preparation process, the weight-volume ratio of the compound to the solvent is 1 g:1-6 mL.

In some embodiments of the present disclosure, provided is a process for preparing the Crystal Form B of the compound as shown in formula (I), comprising:
(1) adding the compound as shown in formula (I) into a solvent with complete dissolution;
(2) adding amino acid; stirring at 40° C. for 12-24 hours; and filtering to give the Crystal Form B of the compound of formula (I);
wherein,
the solvent is selected from the group consisting of tetrahydrofuran;
the amino acid is selected from the group consisting of L-arginine.

Also provided is use of the crystal forms for the manufacture of a medicament for treating a disease related to $ET_A$ receptor antagonists.

In some embodiments of the present disclosure, the use is characterized in that, the $ET_A$ receptor antagonist-related medicament is a medicament for indications such as pulmonary hypertension, essential hypertension, refractory hypertension, diabetic nephropathy and intracranial vasospasm, etc.

General Definition

Unless stated otherwise, the terms and phrases used herein have the following meaning. A specific term or phrase shall not be considered as indefinite or unclear when it is not specifically defined. It should be understood according to the general meaning. The trade name used herein refers to the corresponding product or the active ingredient.

The intermediate compounds can be prepared through various synthesis processes well-known to a person skilled in the art, including the specific embodiments illustrated below, the embodiments through combination of such specific embodiments with other chemical synthesis processes as well as equivalents well-known to a person skilled in the art. The preferable embodiments comprise but not limited to the Examples herein.

The chemical reaction of the specific embodiments is performed in a suitable solvent, and the solvent should be suitable for the chemical changes of the present disclosure and the required reagents and materials. To obtain the compound of the present disclosure, a person skilled in the art can modify or select a synthesis step or a reaction scheme based on the available embodiments.

The present disclosure will be specifically described hereinafter by Examples. The Examples should be not interpreted as limitation to the present disclosure.

The solvents used herein are commercially available and can be used without further purification.

The solvents used in the present disclosure are commercially available. The following abbreviations are used: ACN for acetonitrile; DCM for dichloromethane; DMF for N,N-dimethylformamide; DMSO for dimethylsulfoxide; EtOH for ethanol; MeOH for methanol; TFA for trifluoroacetic acid; ATP for adenosine triphosphate; HEPES for 4-hydroxyethyl piperazine ethanesulfonic acid.

Technical Effect

The crystal forms of the compound of the present disclosure has good stability and promising druggability. The compounds of the present disclosure all exhibit extremely high in vitro antagonistic activity against the human $ET_A$ receptor, as well as $ET_A/ET_B$ selectivity of over 10,000-fold. The compound of the present disclosure was superior to the control Macitentan in characterization experiments of PXR-mediated induction of CYP3A expression. The compound of the present disclosure was superior to Macitentan in the characterization experiments of the inhibition of all the five major isozymes of human liver microsomal cytokine P450. The compound of the present disclosure exhibits much weaker inhibitory effect on bile salt export pump than Macitentan, thereby significantly reducing the risk of producing hepatotoxicity. The compound of the present disclosure have a good in vivo pharmacokinetic profile both in SD rats and Beagle dogs.

1.1 X-Ray Powder Diffractometer (XRPD)
    Instrument type: Bruker D8 advance X-ray diffractometer
    Testing method: about 10-20 mg of sample is used for XRPD detection.
    Detailed XRPD parameters are as follows:
    Light tube: Cu, kα, (λ=1.54056 Å).
    Light tube voltage: 40 kV, Light tube current: 40 mA
    Divergence slit: 0.60 mm
    Detector slit: 10.50 mm
    Anti-scatter slit: 7.10 mm
    Scanning range: 4-40 deg
    Step size: 0.02 deg
    Time/step: 0.12 s
    Sample stage spinning speed: 15 rpm
1.2 Differential Scanning Calorimeter (DSC)
    Instrument type: TA Q2000 Differential Scanning Calorimeter
    Testing method: The sample (about 1 mg) is placed in DSC aluminum pot for testing, under 50 mL/min $N_2$, with the heating rate of 10° C./min, and the sample is heated from 25° C. to 350° C.
1.3 Thermal Gravimetric Analyzer (TGA)
    Instrument type: TA Q5000IR Thermal Gravimetric Analyzer
    Testing method: The sample (2-5 mg) was placed in TGA platinum pot for testing, under 25 mL/min $N_2$, with the heating rate of 10° C./min, and the sample is heated from room temperature to 350° C.
1.4 Hygroscopicity Test
    The hygroscopicity test of Crystal Form A of the compound of formula (I) of the present disclosure is performed according to the Guidelines for Stability Testing of APIs and Formulations (Chinese Pharmacopoeia 2015 Edition, Volume IV, General Principles).

Categorization in the hygroscopicity evaluation is as follows:

| Hygroscopicity categorization | ΔW % |
|---|---|
| Deliquescence | Absorbs sufficient water to form a liquid |
| Highly hygroscopic | ΔW % ≥ 15% |
| Hygroscopic | 15% > ΔW % ≥ 2% |
| Slightly hygroscopic | 2% > ΔW % ≥ 0.2% |
| Non- or almost non-hygroscopic | ΔW % < 0.2% |

Note:
ΔW % represents the percentage of moisture-absorption weight gain of the test article at 25° C. in a desiccator with a saturated solution of ammonium chloride in the lower part 1.5 High Performance Liquid Chromatographic Analytical Method See Table 3 below for chromatographic conditions for the HPLC method of solid stability testing:

TABLE 3

| Chromatographic column | Waters Xbridge C18, 4.6 mm × 150 mm, 3.5 μm, (PN: 186003034) |
|---|---|
| Wave length | 220 nm |
| Column temperature | 35° C. |
| Flow Rate | 0.8 mL/min |
| Injection temperature | No temperature control |
| Injection volume | 10 μL |
| Mobile phase | A: pH 9.0 10 mmol/L ammonium acetate buffer solution<br>B: ACN |

| | Time (minutes) | A % | B % |
|---|---|---|---|
| Mobile phase procedure | 0.0 | 90 | 10 |
| | 10.0 | 90 | 10 |
| | 30.0 | 40 | 60 |
| | 40.0 | 20 | 80 |
| | 45.0 | 20 | 80 |
| | 45.1 | 90 | 10 |
| | 55.0 | 90 | 10 |

| Data acquisition time | 60 minutes |
|---|---|
| Diluter | Acetonitrile:NaOH (V/V) = 1:1 |

EXAMPLES

Figure 1:
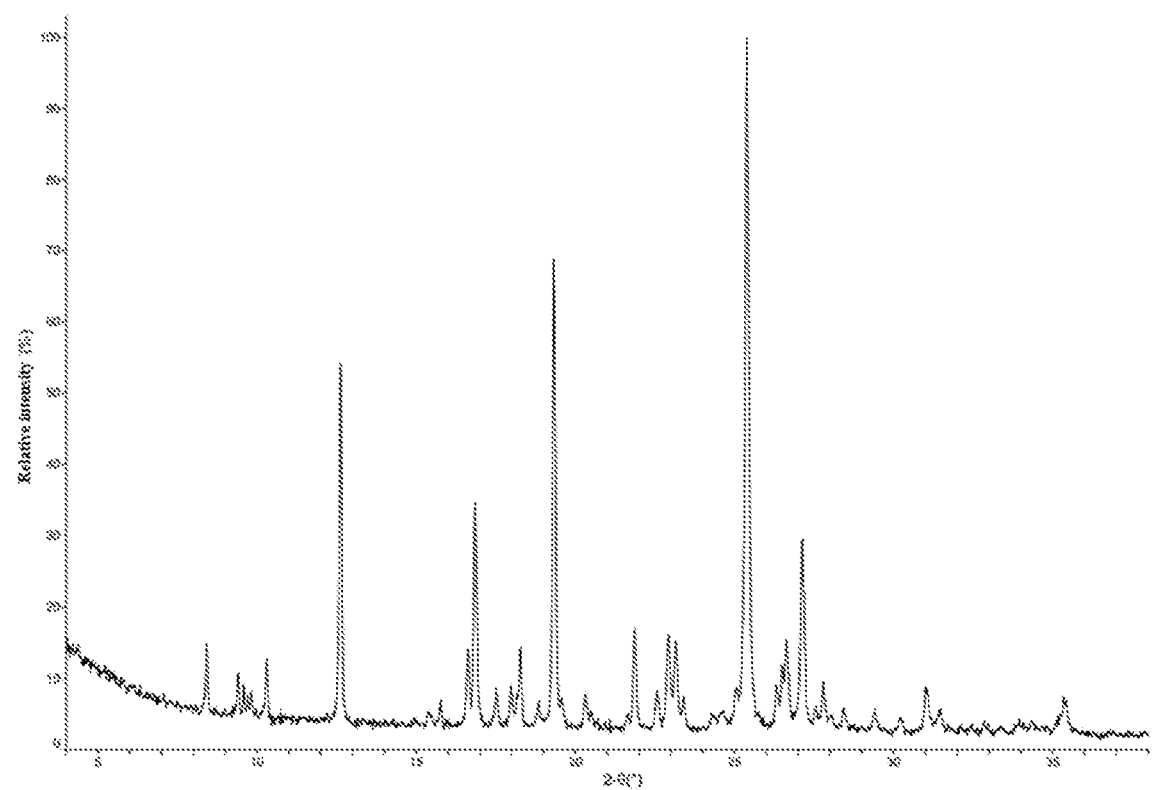
FIG. 1 shows the XRPD spectrum by Cu-Kα radiation of Crystal Form A of the compound of formula (I).
Figure 2:
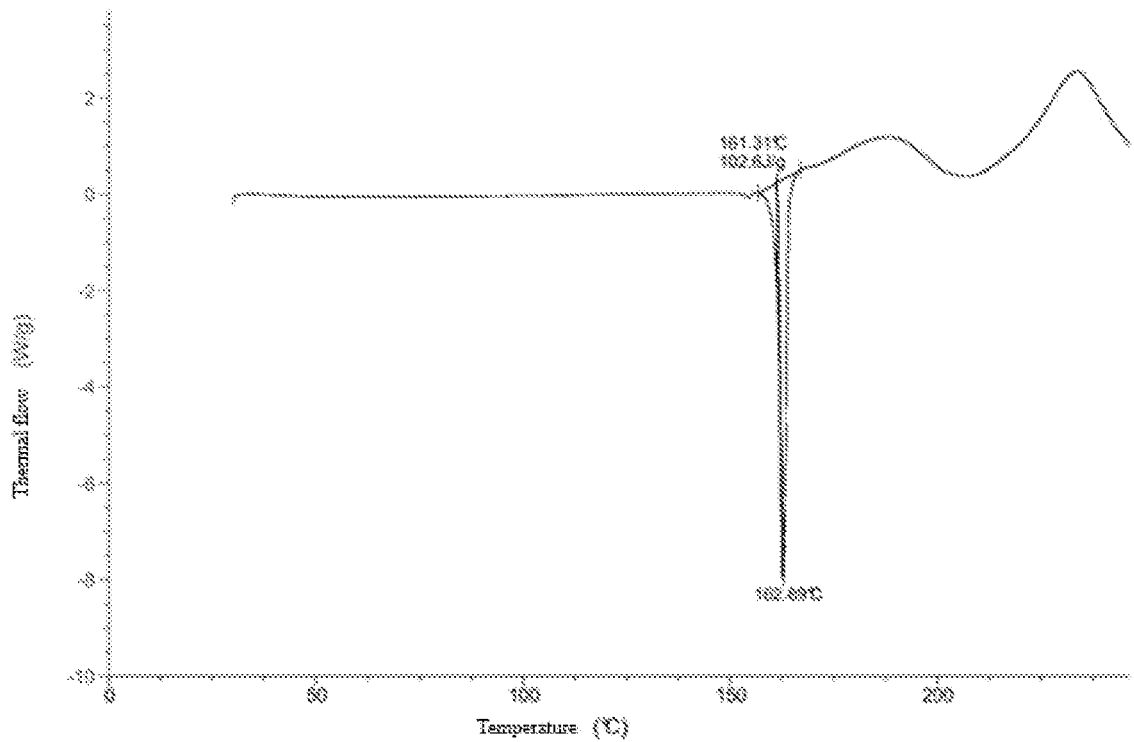
FIG. 2 shows the DSC spectrum of the Crystal Form A of the compound of formula (I).
Figure 3:
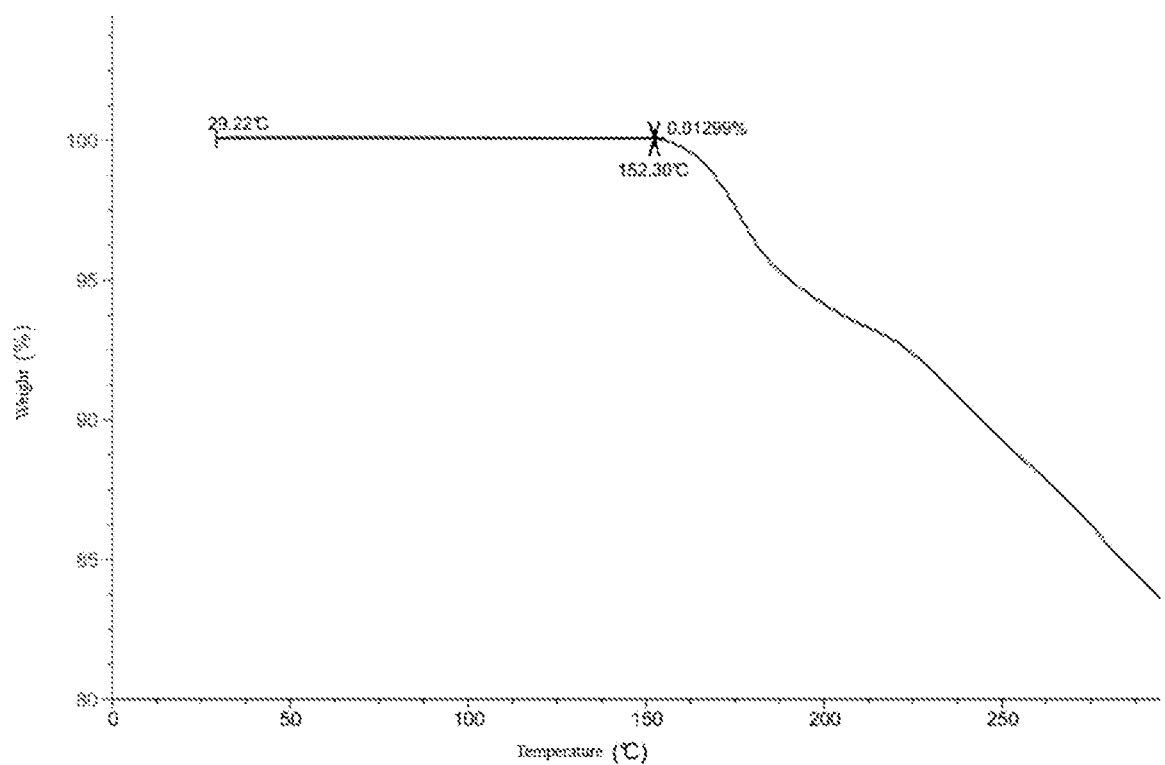
FIG. 3 shows the TGA spectrum of the Crystal Form A of the compound of formula (I).

The following Examples are provided for further illustration for the purpose of better understanding of the present disclosure. The specific embodiments should not be interpreted as limitation to the present disclosure.

Example 1: Preparation of the Compound of Formula (I)

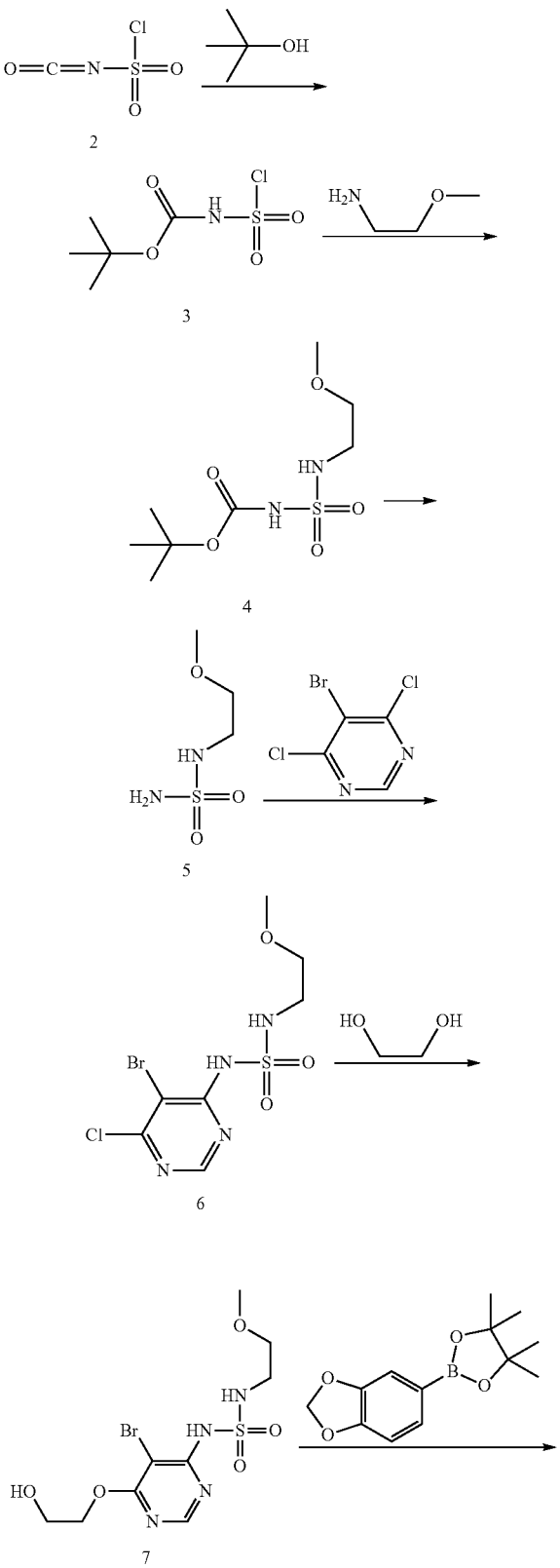

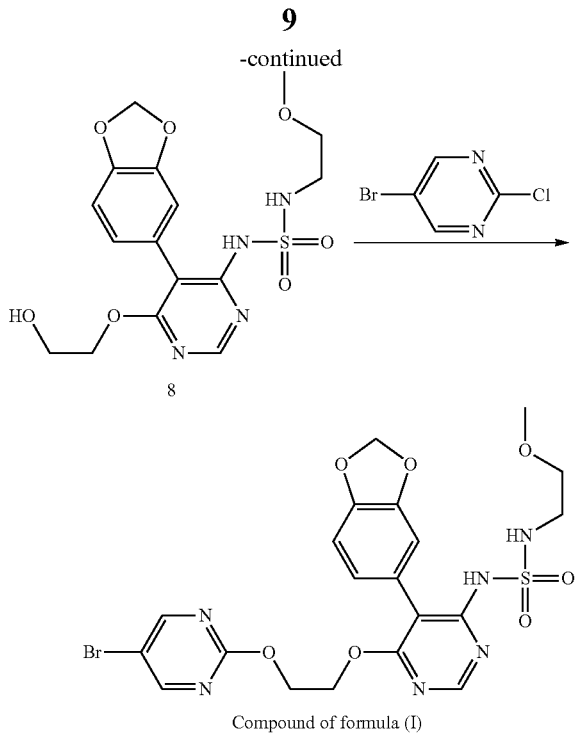

Step 1: Synthesis of Compound 3

Compound 2 (1275 g, 9.01 mol) was dissolved in dichloromethane (5.5 L) at 5-10° C. under nitrogen protection. tert-Butanol (801.23 g, 10.81 mol) was slowly added dropwise at a controlled temperature of 15-20° C. to the solution (dropwise addition during about 2 hr). The reaction mixture was stirred at room temperature for 4 hours. The target compound 3 (crude) was kept in the reaction solvent dichloromethane (5.5 L) and used directly in the next step of the reaction.

Step 2: Synthesis of Compound 4

Compound 2-methoxyethylamine (676.74 g, 9.01 mol) was dissolved in dichloromethane (2.0 L) at 5-10° C. under nitrogen protection. Then triethylamine (1823.44 g, 18.02 mol) was added. The internal temperature was maintained at 10-15° C., and a solution of compound 3 in dichloromethane (9.01 mol, 5.5 L) was slowly added dropwise to the reaction solution (dropwise addition during about 2 hr). The reaction mixture was allowed to warm to room temperature and stirred for 12 hours. After the reaction was complete, 2 M dilute hydrochloric acid was added to the reaction solution to adjust the pH to 3-4. The water layer was separated and discarded. The organic phase was washed with water (2 L×2), dried over anhydrous sodium sulphate and filtered. The filtrate was concentrated under reduced pressure to give the target compound 4. $^1$H NMR (400 MHz, CDCl$_3$) δ: 7.24 (br s, 1H), 5.45 (t, J=5.6 Hz, 1H), 3.53 (t, J=5.0 Hz, 2H), 3.37 (s, 3H), 3.26 (q, J=5.4 Hz, 2H), 1.51 (s, 9H).

Step 3: Synthesis of Compound 5

Compound 4 (1912.50 g, 7.52 mol) was added to water (7.0 L) at 5-10° C. The reaction mixture was heated to 90-95° C. and stirred for 4 hours. After cooling to room temperature. Extraction was performed with ethyl acetate (2.0 L×2). The aqueous phase was collected. The organic phase was combined and washed with water (2.0 L). The organic phase was separated and discarded. The two aqueous phases were combined and concentrated under reduced pressure to give the target compound 5. $^1$H NMR (400 MHz, CDCl$_3$) δ: 5.38-5.35 (m, 3H), 3.54 (t, J=5.1 Hz, 2H), 3.36 (s, 3H), 3.30-3.26 (m, 2H).

Step 4: Synthesis of Compound 6

Compound 5 (609.05 g, 3.95 mol) was dissolved in dimethyl sulfoxide (5.0 L) at 5-10° C. under nitrogen protection. Then potassium tert-butoxide (1107.51 g, 9.87 mol) was added and the reaction mixture was stirred at 15-20° C. for 1 h. A solution of 5-bromo-4,6-dichloropyrimidine (750.03 g, 3.29 mol) in dimethyl sulfoxide (2.0 L) was slowly added dropwise to the reaction solution (dropwise addition during about 2 hr) and the reaction mixture was stirred for another 12 h at room temperature. Two batches of reaction were performed in parallel at the same scale, and then combined for work-up. After the reaction was complete, the reaction solution was poured into cold water (42 L). The pH was adjusted to 3-4 with 2 M dilute hydrochloric acid. Extraction was conducted with ethyl acetate (20 L×4). The organic phases were combined, washed with saline (15 L), dried over anhydrous sodium sulphate, and filtered. The solvent was removed from the filtrate under reduced pressure. The resulting crude product was slurried with methanol (1.2 L) and stirred for 30 minutes, filtered and the filter cake was washed with methanol (100 mL×2). The filter cake was collected and the solvent was remove under reduced pressure to give the target compound 6. $^1$H NMR (400 MHz, CDCl$_3$) δ: 8.50 (s, 1H), 7.80 (s, 1H), 5.89 (t, J=5.6 Hz, 1H), 3.41 (t, J=5.0 Hz, 2H), 3.21-3.17 (m, 5H).

Step 5: Synthesis of Compound 7

At 5-10° C. under nitrogen protection, potassium tert-butoxide (195.25 g, 1.74 mol) was added to ethylene glycol (1.6 L). The reaction mixture was heated to 40° C. and stirred for 1 h. Then compound 6 (200.80 g, 0.58 mol) and ethylene glycol dimethyl ether (100.00 mL) were added sequentially to the solution. The reaction solution was heated to 110° C. and stirred for another 12 hours. After the reaction was complete, the reaction was cooled to room temperature, and the reaction solution was poured into ice water (6.5 L). The pH was adjusted to 3-4 with 2 M dilute hydrochloric acid. Extraction was conducted with ethyl acetate (2.5 L×4). The organic phases were combined, washed with saline (2.0 L×2), dried over anhydrous sodium sulphate, and filtered. The solvent was removed from the filtrate under reduced pressure. The resulting residue was slurried with a mixed solvent of petroleum ether (250 mL) and ethyl acetate (200 mL) at room temperature for 20 minutes, and filtered. The filter cake collected and dried under vacuum to give the target compound 7. $^1$H NMR (400 MHz, CDCl$_3$) δ: 8.38 (s, 1H), 7.67 (s, 1H), 6.00 (t, J=5.8 Hz, 1H), 4.58 (t, J=4.5 Hz, 2H), 3.98 (t, J=4.5 Hz, 2H), 3.49 (t, J=5.0 Hz, 2H), 3.26 (s, 3H), 3.25-3.21 (m, 2H), 2.45 (br s, 1H).

Step 6: Synthesis of Compound 8

Compound 7 (108.02 g, 0.29 mol), 3,4-dimethylenedioxyphenylboronic acid pinacol ester (94.27 g, 0.38 mol) and cesium carbonate (283.46 g, 0.87 mol) were dissolved in a mixed solvent of dioxane (2.10 L) and water (210 mL) at 5-10° C. under nitrogen protection. Then [1,1'-bis(diphenylphosphino)ferrocene]palladium dichloride (32.20 g, 0.044 mol) was added and the reaction mixture was heated to 85° C. and stirred for 15 hours. After the reaction was complete, the reaction was cooled to room temperature, and the solvent was removed under reduced pressure, and added to cold water (3.0 L). The pH was adjusted to 3-4 with dilute hydrochloric acid. Extraction was conducted with ethyl acetate (1.2 L×4). The organic phases were combined, washed with saline (1.50 L), dried over anhydrous sodium sulphate, and filtered. The solvent was removed from the filtrate under reduced pressure. The resulting residue was separated by column chromatography (eluent: dichloromethane/methanol=100/0-100/1, v/v) to give the target compound 8. MS-ESI m/z: 413.0 [M+H]$^+$.

Step 7: Synthesis of the Compound of Formula (I)

Sodium hydride (29.89 g, 0.75 mol, purity: 60%) was added into anhydrous tetrahydrofuran (1.40 L) in batches at 5-10° C. under nitrogen protection. Then anhydrous tetrahydrofuran (500 mL) solution of compound 8 (63.05 g, 0.15 mol) was added into the reaction solution. The reaction mixture was stirred at 5-10° C. for 1 hour. Then 5-bromo-2-chloropyrimidine (44.49 g, 0.23 mol) and anhydrous N,N-dimethylformamide (63 mL) were added sequentially and the reaction mixture was heated to 70-75° C. and the reaction was stirred for another 4 hours. After the reaction was complete, the reaction mixture was cooled to room temperature, and slowly poured into a cold saturated ammonium chloride solution (6.0 L). The pH was adjusted to 3-4 with 2 M dilute hydrochloric acid. Extraction was conducted with ethyl acetate (1.5 L×4). The organic phases were combined, washed with saline (2.0 L), dried over anhydrous sodium sulphate, and filtered. The solvent was removed from the filtrate under reduced pressure. The resulting crude product was dissolved in a mixed solvent of dichloromethane (70 mL) and methanol (240 mL) and refluxed with stirring for 1 h. The heating was turned off and the mixture stirred at 5-10° C. for 12 h. The mixture was filtered and the filter cake was collected. The filter cake was dissolved with dichloromethane (200 mL). Activated carbon (20 g) was added. The mixture was stirred at room temperature for 3 h, and filtered. The solvent was removed from the filtrate under reduced pressure. The resulting residue was slurried with a mixed solvent of dichloromethane (70 mL) and methanol (240 mL) for 12 h, and filtered. The filter cake was collected, washed with methanol (20 mL) and dried under vacuum to give the compound of formula (I). MS-ESI m/z: 568.9 [M+H]$^+$, 570.9 [M+H+2]$^+$. $^1$H NMR (400 MHz, CDCl$_3$) δ: 8.49 (s, 2H), 8.45 (s, 1H), 7.01 (s, 1H), 6.87-6.85 (m, 1H), 6.71-6.69 (m, 2H), 6.05-6.02 (m, 3H), 4.73-4.71 (m, 2H), 4.65-4.63 (m, 2H), 3.49 (t, J=5.0 Hz, 2H), 3.29 (s, 3H), 3.19-3.15 (m, 2H).

Example 2: Preparation of Crystal Form A of the Compound of Formula (I)

The compound of formula (I) (168.00 g, 0.30 mol) was added to acetonitrile (1.85 L) at 10-20° C. The mixture was heated to 75-85° C. and stirred for 2 hours until the solution became clear. The activated carbon (100.05 g) was added to the mixture, which was stirred at 75-85° C. for 3 hours. The mixture was filtered through 50.01 g of diatomite while still hot and the filtrate was stirred for 15 hours to cool naturally to room temperature of 10-20° C. (a large amount of solids precipitated). The mixture was filtered and the filter cake was washed with acetonitrile (100 mL×3). The filter cake was collected and dried under vacuum in a vacuum drying oven to give the Crystal Form A of the compound of formula (I).

About 50 mg of the compound of formula (I) was weighed and added into a 1.5 mL HPLC vial. 400 μL of tetrahydrofuran was added. Mixed well with sonication. The suspension sample was stirred on a magnetic stirrer (40° C.) under protection from light for 48 h. The solid was collected by centrifugation and then dried overnight (16-24 h) in a vacuum drying oven at 30° C. to obtain the Crystal Form A of the compound of formula (I).

About 50 mg of the compound of formula (I) was weighed and added into a 1.5 mL HPLC vial. 400 μL of acetonitrile was added. Mixed well with sonication. The suspension sample was stirred on a magnetic stirrer (40° C.) under protection from light for 48 hours. The solid was collected by centrifugation and then dried overnight (16-24 hours) in a vacuum drying oven at 30° C. to obtain the Crystal Form A of the compound of formula (I).

Example 3: Solid Stability Test for Crystal Form A of the Compound of Formula (I)

According to the Guideline for Stability Testing of APIs and Formulations (Chinese Pharmacopoeia 2015 Edition, Volume IV, General Principles 9001). The stability of Crystal Form A of the compound of formula (I) was examined under conditions of: high temperature (60° C., open), high humidity (room temperature/92.5% relative humidity, open), accelerated conditions (25° C./60% relative humidity, 40° C./75% relative humidity, sealed), and strong light (4500±500 lux, 90 μw/cm$^2$, sealed).

1.5 g of the Crystal Form A of the compound of formula (I) was weighed and added onto an open Petri dish and spread into a thin layer. After being placed under high temperature and high humidity conditions, samples were placed in a desiccator for examination. On the 5$^{th}$, 10$^{th}$ and 30$^{th}$ days, samples were taken for testing, and the results were compared with the initial test results on day 0. Samples placed under strong light condition were covered with a transparent lid and sealed with a sealing film and samples were taken on the 5$^{th}$ and 10$^{th}$ for testing and the results were compared to the initial test results on day 0. Aliquots of 2.0 g of the Crystal Form A of the compound of formula (I) was weighed. Each aliquot was placed in a double-layer LDPE bag. Each layer of LDPE bag was sealed by tying, respectively. Then the LDPE bag was placed in an aluminum foil bag and heat sealed and placed at 25° C./60% relative humidity. Samples were taken at the 3$^{th}$ month, 6$^{th}$ month, 9$^{th}$ month and 12$^{th}$ month, and placed under 40° C./75% relative humidity. Samples were taken at the 1$^{st}$ month, 2$^{ed}$ month, 3$^{th}$ month and 6$^{th}$ month, respectively. The test results were compared with the initial test results on day 0. The test results are shown in Table 4 below.

TABLE 4

Results of solid stability tests on Crystal Form A of the compound of formula (I) at high temperature, high humidity and strong light conditions

| Test conditions | Sampling time points | Appearance | Crystal Form | Crystal Form A of the compound of formula (I) (%) | Total impurities (%) |
|---|---|---|---|---|---|
| — | 0 day | White powder | Crystal Form A | 99.2% | 0.26% |
| High temperature (60° C., open) | 5 days | White powder | — | 100.1% | 0.30% |
| | 10 days | White powder | — | 100.0% | 0.31% |
| | 30 days | White powder | — | 99.1% | 0.14% |
| High humidity (room temperature/ | 5 days | White powder | — | 99.7% | 0.30% |
| 92.5% relative humidity, open) | 10 days | White powder | — | 99.5% | 0.31% |
| | 30 days | White powder | — | 99.5% | 0.15% |
| Strong light (4500 ± 500 lux-hr, | 5 days | White powder | — | 99.7% | 0.29% |
| 90 µw-hr/cm$^2$, sealed) | 10 days | White powder | — | 99.6% | 0.30% |
| 40° C., 75% relative humidity, | 1 month | White powder | — | 99.2% | 0.14% |
| sealed | 2 months | White powder | — | 99.3% | 0.14% |
| | 3 months | White powder | Crystal Form A | 100.6% | 0.13% |
| | 6 months | White powder | Crystal Form A | 100.2% | 0.20% |
| 25° C./60% relative humidity, | 3 months | White powder | Crystal Form A | 100.2% | 0.13% |
| sealed | 6 months | White powder | Crystal Form A | 100.1% | 0.20% |
| | 9 months | White powder | — | 100.0% | 0.13% |
| | 12 months | White powder | — | 100.1% | 0.16% |

"—": not determined.

Conclusion: Crystal Form A of the compound of formula (I) had good stability under high temperature, high humidity or strong light condition.

Example 4: Stability Test of Crystal Form A of the Compound of Formula (I) in Different Solvents The crude compound of formula (I) was dissolved in dichloromethane at 38-40° C., filtered while hot, concentrated under reduced pressure to dryness to obtain mixed crystals of formula (I). Saturated solutions of mixed crystals of the compound of formula (I) in THF and ACN were prepared at 50° C., respectively.

For each of Crystal Form A and Crystal Form B of the compound of formula (I), an about 5 mg sample was weighed and added to saturated solutions in different solvents at different temperatures according to the table below, and placed in a mixer at the corresponding temperature and then stirred for 3 days.

The suspension was centrifuged. The precipitate was taken and dried overnight in a vacuum oven at 30° C. The dried product was subjected to XRPD to determine the status of the crystal forms. The results are shown in Table 5.

Example 5: Study of Hygroscopicity of Crystal Form A of the Compound of Formula (I)

Experimental Methods:
1) Two dry stoppered glass weighing bottles (50 mm external diameter, 30 mm high) were taken and kept in a desiccator with a saturated solution of ammonium chloride in the lower part. The weighing bottles were left open. The lid of the desiccator was closed and the desiccator was placed in a constant temperature room at 25° C. overnight.
2) The weighing bottles were allowed to stand overnight and weighed precisely for removal, as $m_1$ 1, $m_1$ 2, $m_1$ 3 respectively.
3) A sample of an appropriate amount of Crystal Form A of the compound of formula (I) was taken and spread in a weighed weighing (the thickness of the sample was 1 mm) and weighed precisely, as $m_2$ 1, $m_2$ 2, $m_2$ 3 respectively.
4) The weighing bottles were left open and kept in the desiccator with the lid in a desiccator with a saturated solution of ammonium chloride in the lower part, The

TABLE 5

Stability tests of crystal form a in different solvents

| No. | Solvent | Temperature (° C.) | Solvent addition (mL) | Status (3 days later) | Crystalline |
|---|---|---|---|---|---|
| 1 | Acetonitrile | 25 | 0.3 | Precipitation | Crystal Form A |
| 2 | Acetonitrile | 50 | 0.3 | Precipitation | Crystal Form A |
| 3 | Tetrahydrofuran | 25 | 0.3 | Precipitation | Crystal Form A |
| 4 | Tetrahydrofuran | 50 | 0.3 | Precipitation | Crystal Form A |

Experimental conclusion: Crystal Form A of the compound of formula (I) had good stability in acetonitrile and tetrahydrofuran at both 25° C. and 50° C.

lid of the desiccator was closed and then the desiccator was placed in a thermostat at 25° C. for 24 hours.
5) After 24 hours, the weighing bottles were capped and then taken out of the desiccator and weighed precisely, as $m_3$ 1, $m_3$ 2, $m_3$ 3.
6) The moisture-absorption weight gain was calculated as follows: Weight gain percentage=100%×$(m_3-m_2)$/$(m_2-m_1)$ The results are shown in Table 6.

TABLE 6

| Samples | $m_1$ (mg) | $m_2$ (mg) | $m_3$ (mg) | Weight gain percentage (%) | Mean (%) |
|---|---|---|---|---|---|
| Crystal Form A of the compound of formula (I) | 35163.24 | 35703.21 | 35703.82 | 0.11 | 0.075 |
| Crystal Form A of the compound of formula (I) | 33118.09 | 33764.59 | 33764.82 | 0.04 | |

Experimental conclusion: The moisture-absorption weight gain of Crystal Form A of the compound of formula (I) is 0.075%, which was less than 0.2%, indicating non- or almost non-hygroscopic.

Example 6: Preparation of Crystal Form B of the Compound of Formula (I)

About 120 mg of the compound of formula (I) was weighed and added into an 8 mL glass vial. 4 mL of tetrahydrofuran was added. Sonication is conducted for complete dissolution. Samples were stirred on a magnetic stirrer (40° C.). Then an equivalent amount of L-arginine was weighed, and stirred for 18 hours. The suspension was centrifuged. The solid was taken and dried under vacuum (16-18 hours, 35° C.) to obtain the Crystal Form B of the compound of formula (I).

Experimental Example 1. In Vitro Testing of the Antagonistic Effects on Human $ET_A$ Receptors Purpose of the Experiment:
The antagonistic activity of the compounds on endogenously expressed human $ET_A$ receptors in SK-N-MC cells was assessed by measuring the effects of the compounds on changes in cytoplasmic $Ca^{2+}$ ion signaling induced by an agonist of human $ET_A$ receptor using a fluorescence assay. The functional activity of the $ET_A$ receptor antagonistic effect was tested at Eurofins-Cerep SA according to current standard operating procedures.

Experimental Protocol:
1. Cells were suspended in Dulbecco's modified Eagle medium solution (DMEM, Invitrogen) supplemented with 1% FCSd and then distributed at a density of 5×10$^4$ cells/well in 384 plates (100 μL/well).
2. Hank's Balanced Salt Solution (HBSS, Invitrogen) supplemented with 20 mM 4-(2-hydroxyethyl) piperazine-1-ethanesulfonic acid (Hepes, Invitrogen) (pH 7.4) was mixed with the fluorescent probe (Fluo4 NW, Invitrogen) and added to each well. Equilibrated with the cells for 60 minutes at 37° C. and then for 15 min at 22° C.
3. The assay plate was placed in a microplate reader (CellLux, PerkinElmer). DMSO solution of the test compound and the positive control in appropriate concentration or HBSS buffer was added. After 5 minutes, 1 nM endothelin-1 or HBSS buffer (basal control) was added. Then the change in fluorescence intensity was measured. The fluorescence intensity is in proportion to the $Ca^{2+}$ ion concentration of the free cytosol.
4. The result was obtained as the percentage inhibition of the control response to 1 nM endothelin-1.
5. The standard positive control was BQ-123 and several concentrations were tested in each experiment and the data was analyzed using Prism to produce a concentration-response curve to calculate the $IC_{50}$ values of the compounds.
6. The results of the experiment are shown in Table 7.

Experimental Example 2: In Vitro Testing of the Antagonistic Effect on Human $ET_B$ Receptors Purpose of the Experiment:
The antagonist activities of the compounds on human $ET_B$ receptors expressed in transfected CHO cells were assessed by measuring the effects of the compounds on changes in cytoplasmic $Ca^{2+}$ ion signaling induced by an agonist of human $ET_B$ receptor using a fluorescence assay. The functional activity of the $ET_B$ receptor antagonistic effect was tested at Eurofins-Cerep SA according to current standard operating procedures.

Experimental Protocol:
1. Cells were suspended in DMEM buffer (Invitrogen) and then distributed at a density of 3×10$^4$ cells/well in 384 plates (100 μL/well).
2. HBSS buffer (Invitrogen) supplemented with 20 mM Hepes (Invitrogen) (pH 7.4) was mixed with the fluorescent probe (Fluo4 Direct, Invitrogen) and added to each well. Equilibrated with the cells for 60 minutes at 37° C. and then for 15 minutes at 22° C.
3. The assay plate was placed in a microplate reader (CellLux, PerkinElmer). DMSO solution of the test compound and the positive control or HBSS buffer in appropriate concentration was added. After 5 minutes 0.3 nM endothelin-1 or HBSS buffer (basal control) was added. Then the change in fluorescence intensity was measured. The fluorescence intensity is in proportion to the $Ca^{2+}$ ion concentration of the free cytosol.
4. The result was obtained as the percentage inhibition of the control response to 0.3 nM endothelin-1.
5. The standard positive control was BQ-788 and several concentrations were tested in each experiment and the data was analyzed using Prism to produce a concentration-response curve to calculate the $IC_{50}$ values of the compounds.

Note: BQ-123 is a selective $ET_A$ endothelin receptor antagonist used as a biochemical tool in endothelin receptor function studies; BQ-788 is a selective $ET_B$ endothelin receptor antagonist used as a biochemical tool in endothelin receptor function studies.

TABLE 7

In vitro antagonistic activity of Crystal Form
A of the compound of formula (I) on human $ET_A$ and
$ET_B$ receptors and its selectivity over $ET_B$

| Test article | $ET_A$ $IC_{50}$ (nM) | $ET_B$ $IC_{50}$ (μM) | $ET_A/ET_B$ Selectivity |
|---|---|---|---|
| Crystal Form A of the compound of formula (I) | 1.6 | 32 | 20000 |
| BQ-123 | 0.61/0.48 | / | / |
| BQ-788 | / | 0.13/0.091 | / |

Note:
"/" means not measured.

Conclusion: Crystal Form A of the compound of formula (I) exhibited very high in vitro antagonistic activity against the human $ET_A$ receptor. The selectivity of Crystal Form A of the compound of formula (I) of the present disclosure for $ET_A$ over $ET_B$ was as high as 20,000-fold.

Experimental Example 3: Human Pregnane X Receptor (PXR) Test

Purpose of the Experiment:
To assess the induction of PXR-mediated CYP3A expression by the compounds.
Experimental Materials and Equipment:

| Name | Source | Type |
|---|---|---|
| DPX2 Cell | Puracyp | / |
| Dosing Media | Puracyp | D-500-100 |
| P450-Glo ™ CYP3A4 Assay and Screening System (Luciferin-IPA & Luciferin Detection Reagent) | Promega | V9001 |
| CellTiter-Fluor ™ Kit (CTF buffer & Assay Buffer) | Promega | G6081 |
| One Glo ™ kit (ONE-Glo ™ Luciferase Assay Buffer & ONE-Glo ™ Assay Substrate) | Promega | E6110 |

Experimental Protocol:
1. The DPX2 cells was thawed under aseptic conditions.
2. The DPX2 cytosol was distributed in 96-well plates (100 μl/well) and placed the plates in a 5% $CO_2$/37° C. incubator overnight.
3. The quantitative feeding medium was thawed in a 37° C. water bath. The positive control rifampicin was thawed at room temperature. A series of the test compound and positive control dilutions were prepared in quantitative feeding medium. The medium was carefully aspirated and discarded from each well, without disturbing the cells during the aspiration process. 100 μl of each concentration of the test compound was transferred to pre-labeled wells. The positive control group and the blank group were processed in the same way. The plates were placed back in the incubator and exposed for 24 hours.
4. Enzyme activity test:
   (1) 7 μl of Luciferin-IPA was added to 7 ml of quantitative feeding medium, inverted to mix, and poured into the Luciferin-IPA reagent tank.
   (2) The 96-well plate was taken out of the incubator and the medium was carefully aspirated from each well. 50 μl of the Luciferin-IPA reagent was added to each well and the cell plate was placed back into the incubator for incubation of 60 minutes.
   (3) During incubation, the P450-Glo buffer was poured into the Luciferin assay reagent and inverted to mix.
   (4) The 96-well plate was taken out of the incubator. 40 μl of solution was transferred from each well to the corresponding white 96-well plate. The corresponding position of each well was kept in line with the original cell plate.
   (5) After transferring the P450-Glo™ solution to the replicate plate, 10 ml of Cell Titration Buffer (CTF buffer) was transferred to a 15 ml sterile conical tube. 5 μl of CellTiter-Fluor™ reagent was added. Inverted to mix.
   (6) Using a multi-channel pipette, 100 μl of CellTiter-Fluor™ reagent was gently added to the 96-well plate in which the cells were originally cultured. The plate was placed back to the incubator for 60 minutes.
   (7) 40 μl of Luciferin detection reagent/P450-Glo buffer was added to each well of the replicate plate, stirred and incubated for 20 minutes at room temperature.
   (8) After incubation with Luciferin detection reagent for 20 minutes, a luminometer (set for 1-5 seconds. Read out time) was used to determine the luminescence of each well of the white 96-well plate. Relatively high gain settings should be used.
   (9) ONE-Glo™ luciferase assay buffer to ONE-Glo™ test reagent was added, inverted to mix.
   (10) After incubation at 37° C. for 60 minutes, the original 96-well plate was taken out of the incubator, the microplate reader was set to fluorescence mode and the excitation wave length was set to 380-400 nm and the emission wave length to 505 nm. The fluorescence intensity of each well was measured.
   (11) The cell plate was removed from the microplate reader. 100 μl of ONE-Glo™ test reagent was added to each well. The plate was shaken to mix and incubated at room temperature for 5 minutes.
   (12) The microplate reader was set to 5 s pre-shake and 5 s well reading. The fluorescence intensity of each well was measured. A high instrument gain (sensitivity) setting should be used.
5. The activation effect of the drug on PXR was reflected by fold induction, i.e. fold induction of each group=luciferase activity value of the drug-treated group/luciferase activity value of the solvent control group. This was used to predict its induction on CYP3A4. The positive control was rifampicin. Six concentrations were tested in each experiment and the data was analyzed using Prism to produce a concentration-response curve to calculate the $EC_{50}$ values of the compounds.

Results:
The test results are shown in Table 8.

TABLE 8

Results of induction of PXR-mediated CYP3A expression by the compound of the present disclosure

| Test compound | Compound of formula (I) | Control compound (Macitentan) |
|---|---|---|
| $EC_{50}$ (μM) | 27.6 ± 1.33* | 6.34 ± 0.170* |

*Calculation error of the simulation curve

Conclusion:

The compound of formula (I) of the present disclosure showed a weak induction of PXR-mediated CYP3A expression while the compound Macitentan showed a strong induction of PXR-mediated CYP3A expression. Therefore, the compound of formula (I) was superior to Marcitetan in the characterization experiments of PXR-mediated induction of CYP3A expression.

Experimental Example 4: Inhibition Assay for Human Liver Microsomal Cytokine P450 Isozymes Purpose of the Experiment:

The aim of the project was to evaluate the inhibitory activity of the test article against human liver microsomal cytochrome P450 isozymes (CYP1A2, CYP2C9, CYP2C19, CYP2D6 and CYP3A4) using a 5-in-1 probe substrate for CYP isozymes.

Experimental Protocol:

Mixed human liver microsomes (HLM) were purchased from Corning Inc. (Steuben, New York, USA) and stored at less than −80° C. prior to use. A diluted series of concentrations of the stock solution of the test article was added to an incubation system containing human liver microsomes, probe substrate and cofactors of the circulatory system. The control without the test article but with solvent was used as the enzyme activity control (100%). The concentration of metabolites generated by the probe substrate in the samples was determined by liquid chromatography-tandem mass spectrometry (LC-MS/MS). A non-linear regression analysis of the mean percentage activity of the test article against concentration was performed using SigmaPlot (V.11). The $IC_{50}$ values were calculated using a three- or four-parameter inverse hyperbolic logarithmic function.

Results:

The test results are shown in Table 9.

TABLE 9

Results of inhibition of the compound of the present disclosure on human liver microsomes cytochrome P450 isozymes

| Compound | P450 isozyme inhibition $IC_{50}$ (μM) | | | | |
|---|---|---|---|---|---|
| | CYP1A2 | CYP2C9 | CYP2C19 | CYP2D6 | CYP3A4-M |
| Control compound (Macitentan) | 37.4 | 7.5 | 31.7 | >50 | 23.0 |
| Compound of formula (I) | 47 | >50 | >50 | >50 | 18 |

Conclusion:

The compound of formula (I) of the present disclosure shows very weak inhibition on all five major isozymes of CYP, while Macitentan shows weak inhibition on four major isozymes of CYP and moderate inhibition on the isozyme CYP2C9. Therefore, the compound of formula (I) was superior to Macitentan in the characterization experiments of the inhibition of the five major isozymes of cytokine P450 in human liver microsomes.

Experimental Example 5: Inhibition Test of the Compounds on Bile Salt Export Pump (BSEP)

Purpose of the Experiment:

In this experiment, the ability of the bile salt export pump (BSEP) to absorb the substrate taurocholic acid TCA was assessed by LC/MS/MS to determine whether the test compound had inhibitory effect on the bile salt export pump transport process.

Experimental Material:

| Name | Source |
|---|---|
| BSEP-Hi5-VT | Solvo Biotechnology |
| | Cat#: SB-BSEP-Hi5-VT |
| 1.0M TRIS Buffer pH 7.4 | Invitrogen |
| | Cat#: 15567-027 |
| Sucrose | Sigma |
| | Cat#: 84100 |
| Tris Base | Sigma |
| | Cat#: T1503 |
| Taurocholic Acid | Sigma |
| | Cat#: T4009 |
| ATP (disodium salt) | Sigma |
| | Cat#: A-2383 |
| 1M HEPES | Gibco |
| | Cat#: 15630-080 |
| AMP (disodium salt) | Sigma |
| | Cat #: 01930 |
| 0.5M EDTA | Biosolution |
| | Cat#: BIO260-15 |
| Methanol | Sigma |
| | Cat#: 494437 |
| Multiscreen 384-well FC filter plates -1.2 micron glass fiber | Millipore |
| | Cat#: MZFCN0W10 |
| ECHO LDV plate | LabCYTE |
| | Cat#: LP-0200 |
| 384-well polypropylene plate | Costar |
| | Cat#: 3656 |
| ECHO 550 | LabCYTE |
| Internal standard | HDBiosciences |

Solution Preparation:

1. Buffer A:

50 mM HEPES pH 7.4, 100 mM $KNO_3$, 10 mM $Mg(NO_3)_2$, 50 mM Sucrose.

2. Buffer B:

10 mM TRIS pH 7.4, 100 mM $KNO_3$, 10 mM $Mg(NO_3)_2$, 50 mM Sucrose.

3. ATP Buffer:

Prepared using Buffer A. 12 ml of Buffer A containing 8.16 mM ATP, 4.08 μM Taurocholic acid.

4. AMP Buffer:

Prepared using Buffer A. 12 ml of Buffer A containing 8.16 mM AMP, 4.08 μM Taurocholic acid.

5. BSEP-Hi5-VT Vesicle Solution:

Prepare a solution containing 5 μg/μL of BSEP-Hi5-VT using Buffer A.

Sample Preparation:
1. Compounds were diluted to 100 mM with DMSO; then subjected to a serial dilution of 3-fold for eleven dilutions. The minimum concentration was 0.169 μM.
2. 20 mM DMSO solution of the positive reference Glyburide (Glibenclamide) was prepared; then subjected to a serial dilution of 2-fold for eleven dilutions. The minimum concentration was 19.5 μM.

Experimental Protocol:
1. ECHO was used to transfer 0.3 μl of DMSO solution of the compounds or diluted DMSO to the corresponding wells of the compounds plate, respectively.
2. 14.7 μl of ATP Buffer was added into the corresponding wells of the compounds and the zero percent effect (ZPE), respectively.
3. 14.7 μl of AMP Buffer was added into the corresponding wells of the hundred percent effect (HPE).
4. The plate was shaken for 10 minutes at 25° C.
5. 15 μl of BSEP-Hi5-VT Vesicle solution was added to each well separately and the plate was shaken for a further 40 minutes at 25° C.
6. 5 μl of 0.5 M Ethylenediaminetetraacetic acid (EDTA) solution was immediately added to each well, followed by 65 μl of Buffer B. All reactions were complete.
7. After the reactions were complete, 95 μl of liquid was transferred from the compounds plate to the filter plate using apparatus.
8. The liquid receiving plate was placed under the filter plate. Then the liquid was removed using a centrifuge. The liquid on the receiving plate was discarded.
9. 90 μl of Buffer B was added to the filter plate. The liquid receiving plate was placed under the filter plate. Then the liquid was removed using a centrifuge. The liquid on the receiving plate was discarded. The filter plate was washed three times in total.
10. The filter plate was left to dry overnight.
11. On the next day, 80 μl of methanol/water (80/20, v/v) solution was added to the filter plate.
12. The plate was vibrated for 15 minutes after applying the film to the filter plate.
13. A new liquid receiving plate was placed under the filter plate and centrifugation was conducted for 5 minutes to filter all the liquid from the filter plate into the receiving plate.
14. 15 μl of internal standard solutions was added to each well of the liquid receiving plate and the plate was sealed with sealing film.
15. Taurocholic acid in the receiving plate was determined using LC/MS/MS.

Several concentrations were tested in each experiment and the data was analyzed using Prism to produce a concentration-response curve to calculate the $IC_{50}$ values of the compounds.

Results:

The results of the test are shown in Table 10.

TABLE 10

Results of the inhibition of the compound of the present disclosure on Bile salt export pump (BSEP)

| Compound | Glibenclamide | Macitentan | Compound of formula (I) |
|---|---|---|---|
| $IC_{50}$ (μM) | 1.489 | 0.47 | 43.77 |

Conclusion:

The compound of formula (I) of the present disclosure exhibits extremely weak inhibitory effect on bile salt export pump (BSEP), On the contrary, Macitentan exhibits strong inhibitory effect. Therefore, the compound of the present disclosure has much weaker inhibitory effect on bile salt export pump than Macitentan, thereby significantly reducing the risk of producing hepatotoxicity.

Experimental Example 6: Pharmacokinetic Evaluation of the Compounds in Rats

Purpose of the Experiment:

The animals used in this study were SD male rats. The LC/MS/MS method was applied to quantify the plasma drug concentrations in rats at different time points after administration of the test compound intravenously or orally by gavage in order to evaluate the pharmacokinetic characteristics of the test compound in rats.

Experimental Material:

Sprague Dawley (SD) rats (male, 200-300 g, 7-10 weeks old, Beijing Vital River or Shanghai SLAC).

Experimental Operations:

A clear solution of the test compound was administered to SD rats by tail vein injection (overnight fasting) or oral gavage (overnight fasting). At 0 hour (before administration through tail vein injection) and 0.0833, 0.25, 0.5, 1, 2, 4, 6, 8 and 24 hours after administration through tail vein injection, 200 μL of blood was collected by jugular venipuncture into anticoagulation tubes supplemented with EDTA-K2 (Jiangsu Kangjian Medical Supplies Co., Ltd.). The mixture in the anticoagulation tube was vortexed thoroughly at 4° C. and then centrifuged at 13,000 rpm for 10 minutes to obtain the plasma. At 0 hours (before administration by oral gavage) and 0.5, 1, 2, 4, 6, 8 and 24 hours after administration by oral gavage, 200 μL of blood was collected by jugular venipuncture into anticoagulation tubes supplemented with EDTA-K2 (Jiangsu Kangjian Medical Supplies Co., Ltd.). The mixture in the anticoagulation tube was vortexed thoroughly and the plasma was then centrifuged at 13,000 rpm for 10 minutes to obtain the plasma. Blood concentrations were determined by LC/MS/MS and the relevant pharmacokinetic parameters were calculated using WinNonlin™ Version 6.3 (Pharsight, Mountain View, CA) pharmacokinetics software with a non-compartmental model linear-log trapezoidal method.

Results:
The results of the test are shown in Table 11.

TABLE 11

Pharmacokinetic parameters of the compound of the present disclosure in rats

| Pharmacokinetic parameters in rats | Intravenous injection (2 mg/kg) | | | Oral (10 mg/kg) | | | |
| --- | --- | --- | --- | --- | --- | --- | --- |
| | Plasma clearance (mL/min/kg) | Half-life (h) | Area under the drug concentration-time curve (μM · h) | Peak concentration (μM) | Peak time (h) | Area under the drug concentration-time curve (μM · h) | Bioavailability (%) |
| Compound of formula (I) | 3.71 | 1.14 | 16.09 | 31.99 | 0.25 | 60.22 | 74.9 |

Conclusion:
The compound of formula (I) had low plasma clearance (<5 mL/min/kg) and high oral gavage bioavailability (>70%) in rats.

Experimental Example 7: Pharmacokinetic Evaluation of the Compounds in Beagle Dogs Purpose of the Experiment:
Male Beagle dogs were used as the test animals in this study. The LC/MS/MS method was applied to quantify the plasma drug concentrations in Beagle dogs at different time points after administration of the test compound by intravenous injection or oral gavage to evaluate the pharmacokinetic profile of the test compound in Beagle dogs.

Experimental Material:
Beagle dogs (Male, 6-15 kg, above 6 months, Beijing Marshall Biotechnology Co.)

Experimental Operations:
A clear solution of the test compound was administered to the Beagle dogs by intravenous injection (overnight fasting) or oral gavage (overnight fasting). At 0 h (before administration by intravenous injection) and at 0.0833, 0.25, 0.5, 1, 2, 4, 6, 8 and 24 h after administration by intravenous injection, about 500 μL of blood was collected from peripheral blood vessels into anticoagulation tubes supplemented with EDTA-K2 (Jiangsu Kangjian Medical Supplies Co., Ltd.). At 0 hours (before administration by oral gavage) and 0.25, 0.5, 1, 2, 4, 6, 8 and 24 hours after administration by oral gavage, about 500 μL of blood was collected from peripheral blood vessels into anticoagulation tubes supplemented with EDTA-K2. The mixture in the anticoagulation tube was vortexed thoroughly at 4° C. and the plasma was then centrifuged at 13,000 rpm for 10 minutes to obtain the plasma. Blood concentrations were determined by LC/MS/MS and the relevant pharmacokinetic parameters were calculated using WinNonlin™ Version 6.3 (Pharsight, Mountain View, CA) pharmacokinetics software with a non-compartmental model linear-log trapezoidal method.

Results:
The results of the test are shown in Table 12.

TABLE 12

Pharmacokinetic parameters according to the compound of the present disclosure in Beagle dogs

| Pharmacokinetic parameters in rats | Intravenous injection (1 mg/kg) | | | Oral (3 mg/kg) | | | |
| --- | --- | --- | --- | --- | --- | --- | --- |
| | Plasma clearance (mL/min/kg) | Half-life (h) | Area under the drug concentration-time curve (μM · h) | Peak concentration (μM) | Peak time (h) | Area under the drug concentration-time curve (μM · h) | Bioavailability F (%) |
| Compound of formula (I) | 4.79 | 0.86 | 7.56 | 12.75 | 0.38 | 33.40 | 147 |

Conclusion:
The compound of formula (I) of the present disclosure had low plasma clearance (<5 mL/min/kg) and high oral gavage bioavailability (>50%) in Beagle dogs.

Experimental Example 8: In Vivo Pharmacodynamic Evaluation of the Compounds

Purpose of the Experiment
The animal model of pulmonary hypertension in SD rats induced by monocrotaline (MCT) was used in this study to examine the pharmacological effects of the test compound on a rat model of pulmonary hypertension.

Experimental Material:
Experimental Animals
  Species: Rat
  Strain: Sprague-Dawley
  Age at arrival at animal house: 5 weeks
  Gender: Male
  Animal weight at the start of the experiment: 200-260 g Number: 88 (81 for pharmacodynamic (PD) and pharmacokinetic (PK) tests and 7 for PK-blank matrix)
Supplier: Shanghai SLAC Experimental Animals Co.
Certificate of the animals: 20170005008695
Other Reagent Information

TABLE 13

Reagent information sheet

| Name | Manufacturers | Batch number | Storage conditions |
|---|---|---|---|
| MCT | Sigma-Aldrich | WXBC5062V | 2-8° C. |
| Tween 80 | Sigma-Aldrich | BCBV8843 | room temperature |
| PEG400 | Sigma-Aldrich | BCBZ7335 | room temperature |
| 4% Paraformaldehyde fixative | Dingguo changsheng biotech CO. LTD | 92H001335 | 4° C. |

Preparation of Key Reagents and Solutions of the Compounds:

20 mg/mL MCT solution: an appropriate amount of MCT was weighed and added to a flask with an appropriate volume. Firstly, MCT was fully dissolved with a small amount of 1 mol/L HCl, then pH was adjusted to 7-7.5 with 10 mol/L NaOH, and finally physiological saline was added to achieve the total volume.

Solvent: 20% PEG 400+0.5% Tween 80 dissolved in deionized water. The pH was adjusted to 9±0.1.

Solutions of 3 mg/mL Macitentan, 0.1 mg/mL, 0.3 mg/mL and 1 mg/mL the compound of formula (I): an appropriate amount of the compound was weighed and added to a flask with an appropriate volume. PEG 400 of 20% of the total volume was added. Heating and stirring were conducted at 40° C. Tween 80 of 0.5% of the total volume was added. Heating and stirring were conducted at 40° C. Deionized water of 70-75% of the volume was added. Heating and stirring were conducted at 40° C. The pH was adjusted with 5 N NaOH until became clear. Then the pH was reversely adjusted to less than 9 with 6 N HCl and 1 N HCl. The remaining volume was made up with deionized water to achieve the total volume. The final pH was determined (9±0.1).

30 mg/mL sodium pentobarbital solution: an appropriate volume of sodium pentobarbital stock solution was measured and added into a flask with an appropriate volume and diluted to final concentration with physiological saline.

Instrument Information:

TABLE 14

Instrument information sheet

| Name | Manufacturers | Type |
|---|---|---|
| Multi-channel physiological signal acquisition and processing system | Chengdu Instrument Factory | RM6240C |
| Small animal ultrasound imaging | VISUALSONICS | Vevo1100 |
| Centrifugal machine | Eppendorf | centrifuge 5417R |

Grouping of Animals

After the animals had been acclimatized for about 1 week, the animals were randomized into 9 groups according to body weight and the condition of the animal, as shown in Table 15.

TABLE 15

Experimental animal grouping and dosing regimen

| Test classification | Group | Group No. | Number of animals | Induction (subcutaneous/ single dose) | Medication/ route/frequency | Administration concentration (mg/mL) | Days of administration (Day) |
|---|---|---|---|---|---|---|---|
| PDTEST | Blank group | G1 | 12 | NS | Vehicle/gavage administration/ once a day | — | 21 consecutive days of administration |
| | Vehicle group | G2 | 12 | MCT | Vehicle/gavage administration/ once a day | — | 21 consecutive days of administration |
| | Macitentan -30 mg/kg | G3 | 12 | MCT | Macitentan/gavage administration/ once a day | 3 | 21 consecutive days of administration |
| | Compound of formula (I) -1 mg/kg | G4 | 12 | MCT | Compound of formula (I)/ PO/QD | 0.1 | 21 consecutive days of administration |
| | Compound of formula (I) -3 mg/kg | G5 | 12 | MCT | Compound of formula (I)/ PO/QD | 0.3 | 21 consecutive days of administration |
| | Compound of formula (I) -10 mg/kg | G6 | 12 | MCT | Compound of formula (I)/ PO/QD | 1 | 21 consecutive days of administration |
| PKTEST | PK-Mac -30 mg/kg | G7 | 3 | MCT | Macitentan/ PO/QD | 3 | 21 consecutive days of administration |
| | PK- Compound of formula (I) -1 mg/kg | G8 | 3 | MCT | Compound of formula (I)/ PO/QD | 0.1 | 21 consecutive days of administration |
| | PK- Compound of formula (I) -3 mg/kg | G9 | 3 | MCT | Compound of formula (I)/ PO/QD | 0.3 | 21 consecutive days of administration |

Note:
Mac represents Macitentan.

Monitoring Indicators

Monitoring Indicators in PD Tests
1) Daily monitoring of the general condition of the animals and their body weights;
2) Right ventricular function tests: right ventricular ejection fraction (RVEF), right ventricular wall thickness (RVWT);
3) Hemodynamic tests: right ventricular systolic pressure (RVSP);
4) Determination of the right ventricular hypertrophy index (RVHI): RV/(LV+SEP);
5) 4-HE staining to observe PAWT/IHC staining to observe PCNA as the endpoint detection.

Monitoring Indicators in PK Tests
1) Daily monitoring of the general condition of the animals and their body weights;
2) Plasma: determination of the pharmacokinetic parameters of the compounds in plasma.

Test Method

B-Mode Ultrasonic Detection of RVEF, RVWT

Rats were anesthetized with 30 mg/mL pentobarbital sodium (2 mL/kg, ip) and RVEF, RVWT were measured using a small animal ultrasound instrument (VEVO-1100).

Measurement of RVSP in Rats by Right Heart Catheterization

Rats were anesthetized with 30 mg/mL sodium pentobarbital (2 mL/kg, ip), fixed onto a surgical plate in supine position, and shaved on the neck. A skin incision was made on the neck. The subcutaneous tissue and muscle layer were bluntly dissected. And the left carotid artery and right jugular vein were stripped. A rat-specific right heart catheter (a PE tube with an external diameter of about 1.5 mm and a small arc-shaped curve at the distal end) connected to a pressure transducer and filled with 0.3% heparin sodium solution was inserted into the right external jugular vein. The arc of the pulmonary artery catheter was kept downwards during the operation and the pulmonary artery catheter was threaded towards the right atrium. The pressure waveform was used to judge whether it had reached the heart. The catheter was deflected towards the left and pushed forward into the right ventricle.

Measurement of RVHI

The heart was removed. The atria and great vessels were removed. Blotted to dryness with filter paper. The right ventricle was stripped and weighed to calculate RVHI=RV/(LV+SEP).

4-HE staining to observe PAWT/IHC staining to observe PCNA as the endpoint detection After euthanasia of the rats, the middle lobe of the right lung was removed, perfused using saline and placed in 4% paraformaldehyde for fixation for the purpose of pathological examination.

Blood Collection and Plasma Preparation

Blood samples were taken before and after dosing on the day of the endpoint, at time points of 0, 0.25, 0.5, 1, 2, 4, 6 and 8 h. The rats were placed in a fixator, 250 μL of blood was collected from the tail vein, transferred to an EP tube with anticoagulant (5-8 μL of 15% EDTA), inverted and shaken, and immediately placed on wet ice for temporary storage. The collected blood samples were placed in centrifugal machines and centrifuged at 4° C., 3000 rpm for 15 min. The plasma was collected after centrifugation and immediately placed on dry ice. After all samples have been collected and transferred to cryopreservation at −80° C. for pharmacokinetic analysis.

Statistical Analysis:

All data was entered into an Excel document and expressed as mean (Mean)±standard error of mean (SEM). One-way ANOVA with Dunnett's t test was used to analyze and compare the data of each group. Differences between two groups were compared using the unpaired two-tailed t-test method. Statistical analysis results P<0.05 were considered significantly different.

Test Results:

TABLE 16

Efficacy of the test compound in rats with pulmonary hypertension (Mean ± SEM, n = 12)

| Groups | 21-day weight change rate (%) | Right ventricular systolic pressure (mmHg) | Right ventricular hypertrophy index | Right ventricular wall thickness (mm) | Right ventricular ejection fraction (%) | PCNA positivity rate (%) | Percentage of middle pulmonary artery intima-media thickness (%) |
|---|---|---|---|---|---|---|---|
| Blank group | 54.31 ± 2.49 | 20.56 ± 0.66 | 0.26 ± 0.01 | 1.01 ± 0.04 | 78.58 ± 1.65 | 2.10 ± 0.40 | 28.98 ± 0.71 |
| Vehicle group | 39.30 ± 1.77*** | 53.91 ± 3.66*** | 0.48 ± 0.03*** | 1.39 ± 0.08*** | 50.45 ± 2.16*** | 6.49 ± 0.86*** | 50.99 ± 1.16*** |
| Mac −30 mg/kg | 45.75 ± 2.14 | 38.71 ± 3.52## | 0.36 ± 0.03### | 1.13 ± 0.04## | 58.87 ± 1.71# | 4.43 ± 0.42 | 46.56 ± 1.07# |
| Compound of formula (I) −1 mg/kg | 43.33 ± 1.56 | 40.72 ± 3.38# | 0.40 ± 0.01# | 1.16 ± 0.05# | 58.48 ± 2.11# | 3.6 ± 0.69## | 40.44 ± 1.13### |
| Compound of formula (I) −3 mg/kg | 41.23 ± 3.47 | 36.70 ± 3.81## | 0.38 ± 0.03## | 1.11 ± 0.05## | 58 ± 1.80# | 3.56 ± 0.66## | 35.44 ± 1.55### |
| Compound of formula (I) −10 mg/kg | 42.04 ± 3.07 | 37.82 ± 3.10## | 0.36 ± 0.02### | 1.10 ± 0.05## | 59.86 ± 2.29## | 2.85 ± 0.65### | 40.11 ± 1.07### |

***P < 0.001, Vehicle vs Sham, t-test;
P < 0.05,
P < 0.01,
P < 0.001 each treatment group vs Vehicle, one-way ANOVA.
Weight change rate (%) Positive values were percentage weight gain and negative values were percentage weight loss.
Mac is Macitentan.

Studies of Pharmacokinetics Accompanying the Efficacy of Formula (I) and Macitentan:

Blood samples were collected before and after dosing on day 21 and collected at time points 0, 0.25, 0.5, 1, 2, 4, 6 and 8 h for analysis of plasma drug concentrations of the compound of formula (I) and Macitentan. The results showed that after administration by gavage at doses of 1 mg/kg and 3 mg/kg, respectively, the area under the drug concentration-time curve ($AUC_{0\text{-}inf}$) of the compound of formula (I) in plasma was respectively 1410 and 5230 ng/mL·h, showing good dose-dependency.

TABLE 17

Pharmacokinetic parameters accompanying the efficacy of the compound of formula (I) and Macitentan in an MCT-induced rat model of pulmonary hypertension (n = 3)

| Pharmacokinetic parameters | Compound of formula (I) administered by gavage 1 mg/kg | | | Compound of formula (I) administered by gavage 3 mg/kg | | | Macitentan administered by gavage 30 mg/kg | | |
|---|---|---|---|---|---|---|---|---|---|
| | Mean | Standard deviation | Coefficient of variation (%) | Mean | Standard deviation | Coefficient of variation (%) | Mean | Standard deviation | Coefficient of variation (%) |
| $C_{max}$ (nM) | 345 | 22.5 | 6.52 | 1120 | 252 | 22.5 | 1840 | 687 | 37.3 |
| $T_{max}$ (h) | 1.00 | 0.00 | 0.00 | 1.00 | 0.00 | 0.00 | 4.08 | 3.88 | 95.1 |
| $T_{1/2}$ (h) | 2.30 | 0.343 | 14.9 | 3.64 | 0.368 | 10.1 | ND | — | — |
| $T_{last}$ (h) | 8.00 | — | — | 8.00 | — | — | 8.00 | — | — |
| $AUC_{0\text{-}last}$ (ng/mL·h) | 1270 | 45.8 | 3.61 | 4220 | 771 | 18.3 | 11000 | 5980 | 54.4 |
| $AUC_{0\text{-}inf}$ (ng/mL·h) | 1410 | 75.7 | 5.37 | 5540 | 730 | 13.2 | ND | — | — |
| $MRT_{0\text{-}last}$ (h) | 2.83 | 0.121 | 4.28 | 3.04 | 0.236 | 7.76 | 4.38 | 0.382 | 8.72 |
| $MRT_{0\text{-}inf}$ (h) | 3.64 | 0.154 | 4.23 | 5.52 | 0.765 | 13.9 | ND | — | — |
| $AUC_{0\text{-}inf}/AUC_{0\text{-}last}$ (%) | 111 | 2.52 | 2.27 | 132 | 8.89 | 6.73 | ND | — | — |

Conclusion:

The results of the study showed that the compound of formula (I) significantly improved the indicators of pulmonary hypertension and right ventricular function in a pulmonary hypertension model: at doses of 1, 3 and 10 mg/kg it significantly reduced right ventricular systolic pressure, improved right ventricular function and inhibited proliferation of pulmonary artery smooth muscle. The compound of formula (I) was effective at 1 mg/kg and its effects at lower doses was comparable to Macitentan at 30 mg/kg.

The invention claimed is:

1. A crystal form of the compound as shown in formula (I),

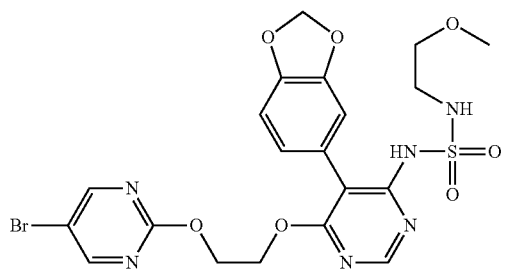

which is selected from the group consisting of:
(1) Crystal Form A, wherein the Crystal Form A has an X-ray powder diffraction, pattern having characteristic diffraction peaks at the following 2θ angles: 12.62±0.20° 16.86±0.20°, 19.33±0.20°, and 25.38±0.20°; and (2) Crystal Form B, wherein the Crystal Form B has an X-ray powder diffraction pattern having characteristic diffraction peaks at the following 2θ angles: 7.51±0.20°, 9.60±0.20°, and 22.56±0.20°.

2. The Crystal Form A according to claim 1, wherein the Crystal Form A has an X-ray powder diffraction pattern having characteristic diffraction peaks at the following 2θ angles: 8.42±0.20°, 10.31±0.20°, 12.62±0.20°, 16.86±0.20°, 18.28±0.20°, 19.33±0.2°, 21.87±0.20°, 25.38±0.20°, and 27.14±0.20°.

3. The Crystal Form A according to claim 2, wherein the Crystal Form A has an X-ray powder diffraction pattern having characteristic diffraction peaks at the following 2θ angles: 8.42°±0.20°, 9.41°±0.20°, 9.58°±0.20°, 9.82°±0.20°, 10.31°±0.20°, 12.62°±0.20°, 15.77°±0.20°, 16.62°±0.20°, 16.86°±0.20°, 17.51°±0.20°, 17.97°±0.20°, 18.28°±0.20°, 18.85°±0.20°, 19.33°±0.20°, 19.58°±0.20°, 20.33°±0.20°, 21.87°±0.20°, 22.58°±0.20°, 22.93°±0.20°, 23.15°±0.20°, 23.39°±0.20°, 25.05°±0.20°, 25.38°±0.20°, 26.31°±0.20°, 26.63°±0.20°, 27.14°±0.20°, 27.79°±0.20°, 29.40°±0.20°, 31.01°±0.20°, 31.48°±0.20°, 35.42°±0.20°, and 39.21°±0.20°.

4. The Crystal Form A according to claim 2, wherein the Crystal Form A has an XRPD pattern as shown in FIG. 1.

5. The Crystal Form A according to claim 1, wherein the Crystal Form A has a differential scanning calorimetry curve having the onset point of an endothermic peak at 161.3±3.0° C.

6. The Crystal Form A according to claim 1, wherein the Crystal Form A has a thermogravimetric analysis curve having a weight loss of 0.01% at 152.3±3.0° C.

7. The Crystal Form B according to claim 1, wherein the Crystal Form B has an X-ray powder diffraction pattern having characteristic diffraction peaks at the following 2θ angles: 7.51±0.20°, 9.60±0.20°, 15.05±0.20°, 19.09±0.20°, 22.56±0.20°, 24.18±0.20°, 24.79±0.20°, and 27.95±0.20°.

8. The Crystal Form B according to claim 7, wherein the Crystal Form B has an X-ray powder diffraction pattern having characteristic diffraction peaks at the following 2θ angles: 7.51°±0.20°, 9.60°±0.20°, 11.08°±0.20°, 15.05°±0.20°, 15.52°±0.20°, 17.53°±0.20°, 18.34°±0.20°, 19.09°±0.20°, 20.41°±0.20°, 20.85°±0.20°, 22.20°±0.20°, 22.56°±0.20°, 23.15°±0.20°, 24.18°±0.20°, 24.79°±0.20°, 27.69°±0.20°, 27.95°±0.20°, 28.75°±0.20°, 33.57°±0.20°, and 35.42°±0.20°.

Figure 4:
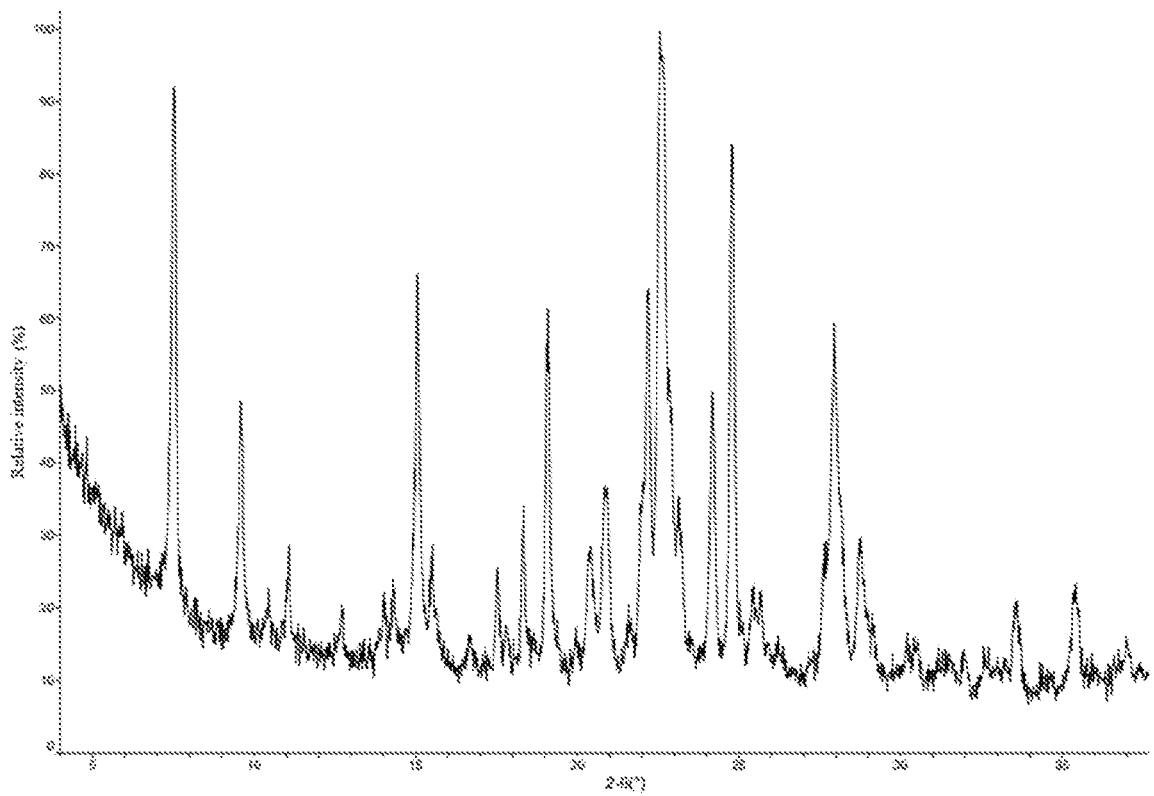
FIG. 4 shows the XRPD spectrum by Cu-Kα radiation of Crystal Form B of the compound of formula (I).
Figure 5:
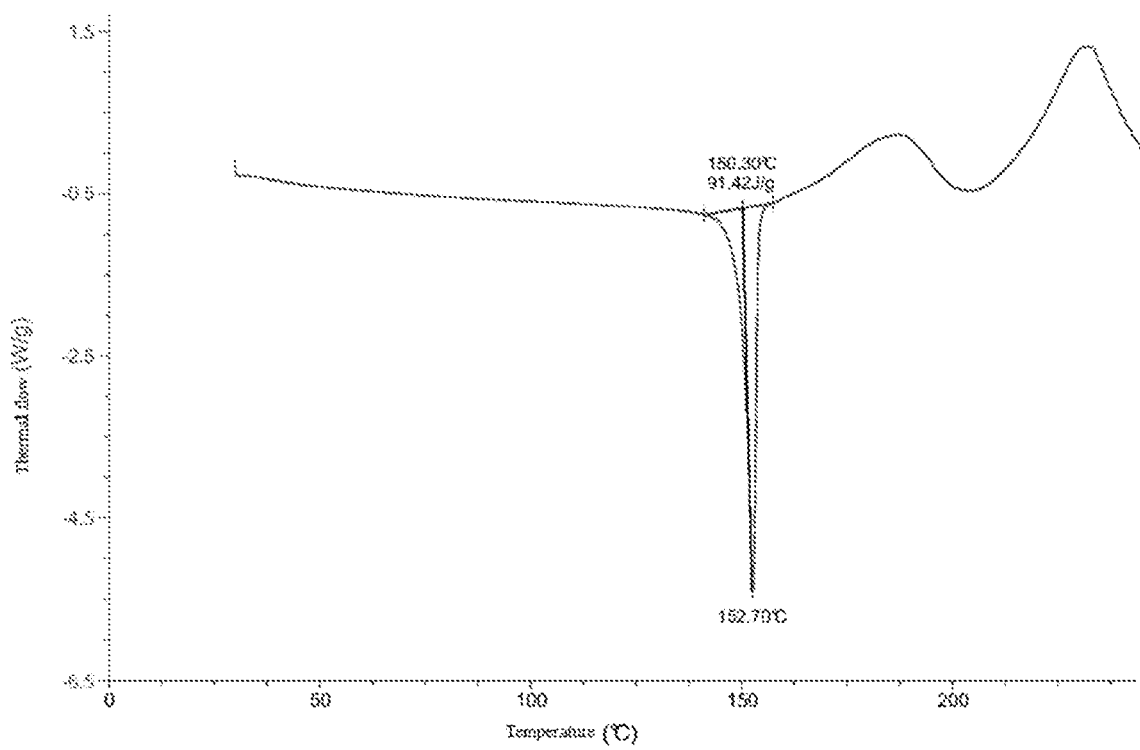
FIG. 5 shows the DSC spectrum of the Crystal Form B of the compound of formula (I).
Figure 6:
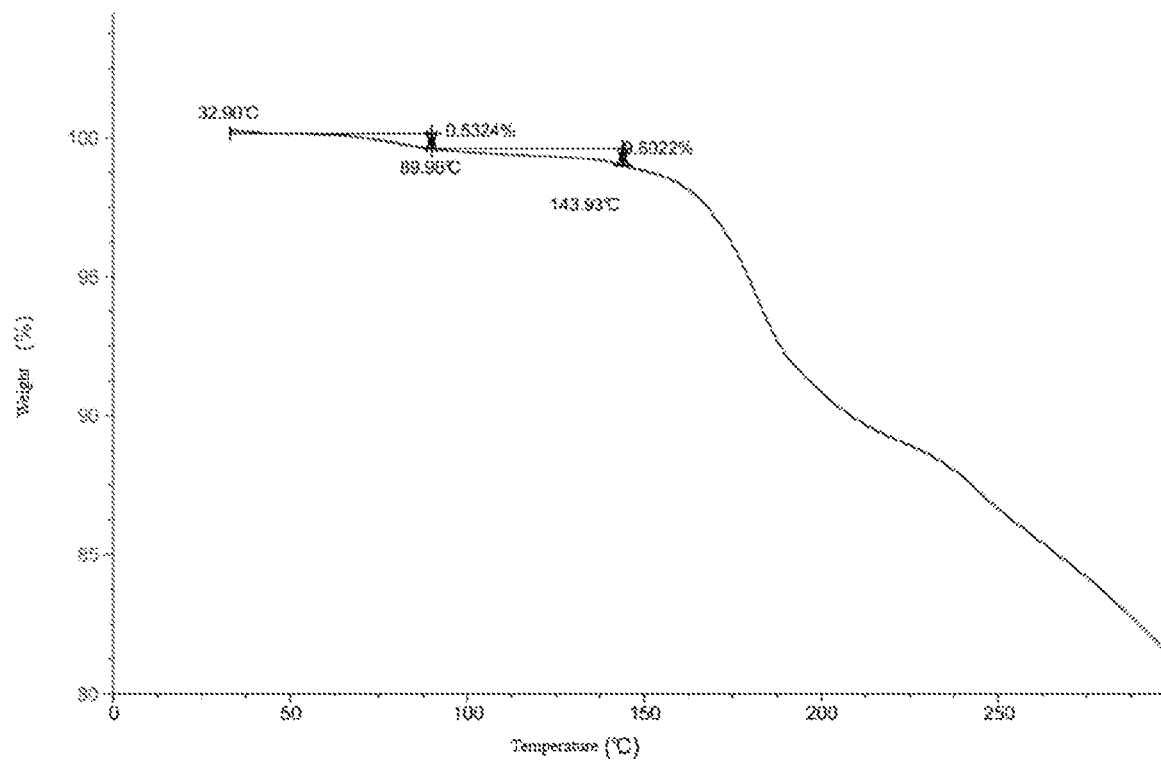
FIG. 6 shows the TGA spectrum of the Crystal Form B of the compound of formula (I).

9. The Crystal Form B according to claim 8, wherein the Crystal Form B has an XRPD pattern as shown in FIG. 4.

10. The Crystal Form B according to claim 1, wherein the Crystal Form B has a differential scanning calorimetry curve having the onset point of an endothermic peak at 150.3±3.0° C.

11. The Crystal Form B according to claim 1, wherein the Crystal Form B has a thermogravimetric analysis curve having a weight loss of 0.53% 90.0±3.0° C., and a further weight loss of 0.60% at 143.9±3.0° C.

12. A process for preparing the Crystal Form A of the compound as shown in formula (I) as defined in claim 1, comprising:
(1) adding the compound as shown in formula (I) into a solvent to obtain a solution, with heating for dissolving;
(2) cooling the solution in step (1) until a solid is precipitated; stirring; and filtering to give the Crystal Form A of the compound of formula (I).

13. The process according to claim 12, wherein the solvent is selected from the group consisting of tetrahydrofuran and acetonitrile.

14. The process according to claim 12, wherein the stirring is conducted at the temperature of 10° C. to 60° C.

15. The process according to claim 12, wherein the stirring time is 12 hours to 24 hours.

16. The process according to claim 12, wherein the weight-volume ratio of the compound to the solvent is 1 g: 1-6 mL.

17. A process for preparing the Crystal Form B of the compound as shown in formula (I) as defined in claim 1, comprising:
(1) adding the compound as shown in formula (I) into a solvent with complete dissolution;
(2) adding an amino acid; stirring at 40° C. for 12-24 hours; and filtering to give the Crystal Form B of the compound of formula (I);
wherein,
the solvent is selected from the group consisting of tetrahydrofuran;
the amino acid is selected from the group consisting of L-arginine.

18. A method for treating a disease related to $ET_A$ receptor antagonist, comprising administering to a subject in need thereof an effective amount of the crystal form according to claim 1;
wherein, the disease related to $ET_A$ receptor antagonist is pulmonary hypertension, essential hypertension, refractory hypertension, diabetic nephropathy or intracranial vasospasm.

19. A pharmaceutical composition comprising a crystal form according to claim 1.

* * * * *